United States Patent
McNaughton et al.

(10) Patent No.: US 9,797,817 B2
(45) Date of Patent: Oct. 24, 2017

(54) MULTI-MODE SEPARATION FOR TARGET DETECTION

(71) Applicant: The Regents of the University of Michigan, Ann Arbor, MI (US)

(72) Inventors: Brandon H. McNaughton, Ann Arbor, MI (US); Paivo Kinnunen, Ann Arbor, MI (US); John G. Younger, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 934 days.

(21) Appl. No.: 13/887,264

(22) Filed: May 3, 2013

(65) Prior Publication Data
US 2013/0337455 A1 Dec. 19, 2013

Related U.S. Application Data

(60) Provisional application No. 61/642,305, filed on May 3, 2012.

(51) Int. Cl.
*G01N 33/553* (2006.01)
*G01N 1/30* (2006.01)
(Continued)

(52) U.S. Cl.
CPC ............ *G01N 1/30* (2013.01); *C12Q 1/6804* (2013.01); *C12Q 1/6816* (2013.01); *G01N 33/54326* (2013.01); *G01N 33/54366* (2013.01)

(58) Field of Classification Search
CPC .......................... C12Q 1/6804; G01N 33/54326
(Continued)

(56) References Cited

U.S. PATENT DOCUMENTS 3,676,679 A    7/1972   Waters
4,778,758 A    10/1988   Ericsson et al.
(Continued)

FOREIGN PATENT DOCUMENTS

WO    WO-00/67037 A2    11/2000
WO    WO-01/14591 A1    3/2001
(Continued)

OTHER PUBLICATIONS

Agayan et al., Optical Manipulation of Metal-Silica Hybrid Nanoparticles, Proceedings of SPIE, 5514:502-513 (2004).
(Continued)

*Primary Examiner* — Chris L Chin
(74) *Attorney, Agent, or Firm* — Marshall, Gerstein & Borun LLP

(57) ABSTRACT

Sandwich separation is based on forming a sandwich complex with a magnetic bead, buoyant bead, and a target. Once a sandwich formation is created, the sandwich can be separated using its dual physical properties, namely magnetism and buoyancy. Sandwich separation is highly specific, allows for removal of the beads that do not have any attached target, and reduces the number of background beads. Sandwich separation can also be used to allow for target detection in raw specimen. Also, improvement of detection capability is accomplished by performing AMBR measurements on a solid interface, where the rotational period speeds up and allows for dramatically reduced time-to-result.

17 Claims, 32 Drawing Sheets

(51) Int. Cl.
*C12Q 1/68* (2006.01)
*G01N 33/543* (2006.01)

(58) Field of Classification Search
USPC .................................................... 436/526
See application file for complete search history.

(56) References Cited

U.S. PATENT DOCUMENTS

| | | | |
|---|---|---|---|
| 5,171,534 A | 12/1992 | Smith et al. | |
| 5,232,839 A | 8/1993 | Eden et al. | |
| 5,252,493 A | 10/1993 | Fujiwara et al. | |
| 5,293,210 A | 3/1994 | Berndt | |
| 5,336,600 A | 8/1994 | Monget | |
| 5,374,527 A | 12/1994 | Grossman | |
| 5,434,056 A | 7/1995 | Monget et al. | |
| 5,516,670 A | 5/1996 | Kuehnle et al. | |
| 5,534,527 A | 7/1996 | Black et al. | |
| 5,593,854 A | 1/1997 | Berndt | |
| 5,716,798 A | 2/1998 | Monthony et al. | |
| 5,770,388 A | 6/1998 | Vorpahl | |
| 5,770,440 A | 6/1998 | Berndt | |
| 5,814,474 A | 9/1998 | Berndt | |
| 5,888,760 A | 3/1999 | Godsey et al. | |
| 5,910,300 A | 6/1999 | Tournier et al. | |
| 5,998,224 A | 12/1999 | Rohr et al. | |
| 5,998,517 A | 12/1999 | Gentle, Jr. et al. | |
| 6,002,817 A | 12/1999 | Kopelman et al. | |
| 6,027,946 A | 2/2000 | Weitschies et al. | |
| 6,096,272 A | 8/2000 | Clark et al. | |
| 6,107,102 A | 8/2000 | Ferrari | |
| 6,143,558 A | 11/2000 | Kopelman et al. | |
| 6,159,686 A | 12/2000 | Kardos et al. | |
| 6,275,031 B1 | 8/2001 | Simmonds | |
| 6,372,485 B1 | 4/2002 | Clark et al. | |
| 6,395,506 B1 | 5/2002 | Pitner et al. | |
| 6,437,563 B1 | 8/2002 | Simmonds et al. | |
| 6,518,747 B2 | 2/2003 | Sager et al. | |
| 6,586,259 B1 | 7/2003 | Mahan et al. | |
| 6,596,532 B1 | 7/2003 | Hyman et al. | |
| 6,597,176 B2 | 7/2003 | Simmonds et al. | |
| 6,632,655 B1 | 10/2003 | Mehta et al. | |
| 6,660,381 B2 | 12/2003 | Halas et al. | |
| 6,777,226 B2 | 8/2004 | Jeffrey et al. | |
| 6,780,581 B2 | 8/2004 | Vesey et al. | |
| 6,825,655 B2 | 11/2004 | Minchole et al. | |
| 6,900,030 B2 | 5/2005 | Pitner et al. | |
| 6,927,570 B2 | 8/2005 | Simmonds et al. | |
| 7,115,384 B2 | 10/2006 | Clark et al. | |
| 7,183,073 B2 | 2/2007 | Hyman et al. | |
| 7,323,139 B2 | 1/2008 | LaBorde et al. | |
| 7,341,841 B2 | 3/2008 | Metzger et al. | |
| 7,547,554 B2 | 6/2009 | Odefey | |
| 7,564,245 B2 | 7/2009 | Lee | |
| 7,575,934 B2 | 8/2009 | Atwood | |
| 7,691,600 B2 | 4/2010 | Mercader Badia et al. | |
| 2002/0150914 A1 | 10/2002 | Andersen et al. | |
| 2003/0012693 A1 | 1/2003 | Otillar et al. | |
| 2003/0076087 A1 | 4/2003 | Minchole et al. | |
| 2003/0124516 A1 | 7/2003 | Chung et al. | |
| 2003/0169032 A1 | 9/2003 | Minchole et al. | |
| 2004/0033627 A1 | 2/2004 | Aytur et al. | |
| 2004/0058458 A1 | 3/2004 | Anker et al. | |
| 2005/0048672 A1 | 3/2005 | Luxton et al. | |
| 2006/0008924 A1 | 1/2006 | Anker et al. | |
| 2006/0040286 A1* | 2/2006 | Mirkin ................ | C12Q 1/6816 435/6.11 |
| 2006/0057578 A1 | 3/2006 | Willner et al. | |
| 2006/0160171 A1 | 7/2006 | Bachur et al. | |
| 2006/0210987 A1 | 9/2006 | Gleich | |
| 2006/0216834 A1* | 9/2006 | Yang ................... | G01N 33/558 436/514 |
| 2007/0020720 A1 | 1/2007 | Colin et al. | |
| 2007/0037225 A1 | 2/2007 | Metzger et al. | |
| 2007/0172899 A1* | 7/2007 | Graham ................ | G01N 33/80 435/7.21 |
| 2007/0205767 A1 | 9/2007 | Xu et al. | |
| 2008/0038769 A1 | 2/2008 | Bernardi et al. | |
| 2008/0220411 A1 | 9/2008 | McNaughton et al. | |
| 2009/0085557 A1 | 4/2009 | Krozer et al. | |
| 2009/0136953 A1 | 5/2009 | Gold et al. | |
| 2009/0269854 A1 | 10/2009 | Kageyama | |
| 2010/0033158 A1 | 2/2010 | Dittmer et al. | |
| 2010/0068755 A1 | 3/2010 | Walsh et al. | |
| 2010/0072994 A1 | 3/2010 | Lee et al. | |
| 2010/0129857 A1 | 5/2010 | Walsh et al. | |

FOREIGN PATENT DOCUMENTS

| | | |
|---|---|---|
| WO | WO-03/019188 A1 | 3/2003 |
| WO | WO-2006/104700 A1 | 10/2006 |
| WO | WO-2007/120095 A1 | 10/2007 |
| WO | WO-2008/075285 A1 | 6/2008 |
| WO | WO-2009/037636 A1 | 3/2009 |
| WO | WO-2010/026551 A1 | 3/2010 |
| WO | WO-2010/041178 A1 | 4/2010 |
| WO | WO-2010/048511 A1 | 4/2010 |
| WO | WO-2011/021142 A1 | 2/2011 |
| WO | WO-2012/027747 A2 | 3/2012 |

OTHER PUBLICATIONS

Anker et al., Magnetically Modulated Optical Nanoprobes, Appl. Phys. Letts., 82:1102-1104 (2003).
Astalan et al., Biomolecular Reactions Studied Using Changes in Brownian Rotation Dynamics of Magnetic Particles, Biosensors and Bioelectronics, 19:945-951 (2004).
Bao et al., Cell and Molecular Mechanics of Biological Materials, Nat. Mat., 2:715-725 (2003).
Behrend et al., Brownian Modulated Optical Nanoprobes, Appl. Phys. Letts., 84:154-156 (2004).
Behrend et al., Microheology with Modulated Optical Nanoprobes (MOONs), J. Magnetism and Magnetic Mats., 293:663-670 (2005).
Bhiladvala et al., Effect of Fluids on the Q Factor and Resonance Frequency of Oscillating Micrometer and Nanometer Scale Beams, Phys. Rev. E, 69:36307-1-36307-5 (2004).
Biswal et al., Micromixing with Linked Chains of Paramagnetic Particles, Anal. Chem., 76:6448-6455 (2004).
Biswal et al., Micromixing with linked chains of paramagnetic particles, Anal. Chem., 76:6448-55 (2004).
Bornhop et al., Advance in contrast agents, reporters, and detection, Journal of Biomedical Optics, 6(2):106-115 (2001).
Boucher et al., Bad bugs, no drugs: no Eskape! An update from the Infectious Diseases Society of America, Clin. Infect. Dis., 48(1):1-12 (2009).
Boucher et al., Epidemiology of methicillin-resistant *Staphylococcus aureus*, Clin. Infect. Dis., 46 Suppl 5:S344-9 (2008).
Cebers, Dynamics of an Active Magentic Particle in a Rotating Magentic Field, Phys. Rev. E., 73:021505-1-021505-5 (2006).
Chu et al., *Staphylococcus aureus* bacteremia in patients with prosthetic devices: costs and outcomes, Am. J. Med., 118(12):1416 (2005).
Connolly et al., Experimental Evaluation of the Magnetic Properties of Commerically Available Magnetic Microspheres, Bio-Medical Materials and Engineering, 15:421-431 (2005).
Crick, The Physical Properties of Cytoplasm. A Study by Means of the Magnetic Particle Method. Part II. Theoretical Treatment, Strangeways Research Laboratory, Cambridge, 505-532 (1950).
Crick, et al., The Physical Properties of Cytoplasm A Study by Means of the Magnetic Particle Method—Part I Experimental, Strangeways Research Laboratory, 37-80 (1949).
Deresinski, Counterpoint: Vancomycin and *Staphylococcus aureus*—an antibiotic enters obsolescence, Clin. Infest. Dis., 44(12):1543-8 (2007).
Ekinci et al., Nanoelectromechanical Systems, Review of Scientific Instruments, 76:061101-1-061101-12 (2005).
Elbez et al., Nanoparticle induced cell magneto-rotation: monitoring morphology, stress and drug sensitivity of a suspended single cancer cell, PLOS One, 6(12):e28475 (2011).

(56) References Cited

OTHER PUBLICATIONS

Elfwing et al., Observing Growth and Division of Large Numbers of Individual Bacteria by Image Analysis, Applied and Environmental Microbiology, 70(2):675-678 (2004).
Fennimore et al., Rotational Actuators based on Carbon Nanotubes, Nature, 424:408-410 (2003).
Fratamico et al., Detection of *Escherichia coli* 0157:H7 using a surface plasmon resonance biosensor, Biotechnology Techniques, 12(7):571-6 (1998).
Fujinami et al., Sensitive detection of bacteria and spores using a portable bioluminescence ATP measurement assay system distinguishing from white powder materials, J. Health Sci., 50:126-32 (2004).
Gfeller et al., Micromechanical oscillators as rapid biosensor for the detection of active growth of *Escherichia coli*, Biosens. Bioelectron., 21(3):528-33 (2005).
Gitterman et al., Order and Choas: Are They Contradictory or Complementary? Eur. J. Phys., 23:119-122 (2002).
Godin et al., Using buoyant mass to measure the growth of single cells, Nat. Methods, 7(5):387-90 (2010).
Gu et al., Using Biofunicational Magnetic Nanoparticles to Capture Gram-Negative Bacteria at an Ultra-Low Concentration, Chemical Communications, 15:1966-1967 (2003).
Hafeli et al., Characterization of Magnetic Particles and Microspheres and Their Magnetophoretic Mobility Using a Digital Microscopy Method, European Cells and Materials, 3:24-27 (2002).
Haukanes et al., Application of Magnetic Beads in Bioassays, Bio-Technology, 11:60-63 (1993).
Horvath et al., Magnetic Dimer Motion Effects in a Rotating Magnetic Field (A Qualitative Model of Magnetoviscosity and Permittivity in Magnetorheological Suspensions), Czech J. Phys., 43:671-681 (1993).
Hulteen et al., Nanosphere Lithography: A Materials General Fabrication Process for Periodic Particle Array Surfaces, J. Vac. Sci. Technol. A., 13:1553-1558 (1995).
Ilic et al., Single Cell Detection with Micromechanical Oscillators, J. Vacuum Sci. & Tech. B: Microelectronics and Nanometer Structures, 19:2825-2828 (2001).
Ilic et al., Virus Detection Using Nanoelectromechanical Devices, Appl. Phys. Lett., 85:2604-2606 (2004).
Ilic et al., Mechanical resonant immunospecific biological detector, Appl. Phys. Lett., 77:450-2 (2000).
Ishiyama et al., Swimming of Magnetic Micro-Machines under a Very Wide-Range of Reynolds Number Conditions, IEEE Trans. Magn., 37(4):2868-2870 (2001).
Jain, Understanding barriers to drug delivery: high resolution in vivo imaging is key, Clinical Cancer Research, 5(7):1605-1606 (1999).
Janssen et al., Controlled torque on superparamagnetic beads for functional biosensors, Biosens. Bioelectron., 24(7):1937-41 (2009).
Jiang et al., A lost-wax approach to monodisperse colloids and their crystals, Science, 291 :453-457 (2001).
Kashevsky, Nonlinear Flow-Particle Interaction in Suspensions of Fine Quasi-Rigid Ferroparticles: A Giant Magnetic Effect of Fluid Rotation, J. Phys. D: Appl. Phys., 34:518-524 (2001).
Kinnunen et al., Monitoring the growth and drug susceptibility of individual bacteria using asynchronous magnetic bea rotation sensors, Biosensors and Bioelectronics, 26(5):2751-5 (2010).
Klevens et al., Changes in the epidemiology of methicillin-resistant *Staphylococcus aureus* in intensive care units in US hospitals, 1992-2003, Clin. Infest. Dis., 42(3):389-91 (2006).
Kneipp et al., Surface-Enhanced Raman Spectroscopy in Single Living Cells Using Gold Nanoparticles , Applied Spectroscopy, 56(2):150-154 (2002).
Korneva et al., Carbon Nanotubes Loaded with Magnetic Particles, Nano Lett., 5:879-884 (2005).
Koskinen et al., Development of a rapid assay methodology for antimicrobial susceptibility testing of *Staphylococcus aureus*, Diagn. Microbiol. Infect. Dis., 62(3):306-16 (2008).
Kumar et al., Duration of hypotension before initiation of effective antimicrobial therapy is the critical determinant of survival in human septic shock, Crit. Care Med., 34(6):1589-96 (2006).
Kurlyandskaya et al., Magnetic Dynabeads Detection by Sensitive Element Based on Giant Magnetoimpedance, Biosensors and Bioelectronics, 20:1611-1616 (2005).
Lapointe et al., Statis and Dynamic Properties of Magnetic Nanowires in Nematic Fluids, J. Appl. Phys., 97:10 (2005).
Lu et al., Nanophotonic Crescent Moon Structures with Sharp Edge for Ultrasensitive Biomolecular Detection by Local Electromagnetic Field Enhancement Effect, Nano Lett., 5:119-124 (2005).
MacDougall et al., Antimicrobial stewardship programs in health care systems, Clin. Microbiol. Rev., 18(4):638-56 (2005).
Mayer et al., Measurement of the Fluorescence Lifetime in Scattering Media by Frequency-Domain Photon Migration , Applied Optics, 38:4930-4938 (1999).
McNaughton et al. Sudden Breakdown in Linear Response of a Rotationally Driven Magnetic Microparticle and Application to Physical and Chemical Microsensing (J. Phys. Chem. B, 110 (38), pp. 18958-18964 (2006).
McNaughton et al., Fabrication of Uniform Half-Shell Magnetic Nanoparticles and Microspheres with Applications as Magnetically Modulated Optical Nanoprobes, arXiv:cond-mat/0506418v1, pp. 1-6 (2005).
McNaughton et al., Physiochemical Microparticle Sensors Based on Nonlinear Magnetic Oscillations, Sensors and Actuators B., 121:330-340 (2007).
McNaughton et al., Compact sensor for measuring nonlinear rotational dynamics of driven magnetic microspheres with biomedical applications, JMMM, 321:1648-52 (2009).
McNaughton et al., Single bacterial cell detection with nonlinear rotation rate shifts of driven magnetic microspheres, Appl. Phys. Lett., 91:224105 (2007).
Melle et al., Structure and dynamics of magnetorheological fluids in rotating magnetic fields, Phys. Rev. E, 61(4):4111-7 (2000).
Merkt et al., Capped Colloids as Light-Mills in Optical Traps, arXiv:cond-mat/0605463v1, pp. 1-10 (2006).
Metzger, Amorphous Whiskers of a Cobalt-Gold Alloy, Nature, 212:176-177 (1966).
Moller et al., Ultrafine particles cause cytoskeletal dysfunctions in macrophages, Toxicology and Applied Pharmacology, 182(3):197-207 (2002).
National Nosocomial Infections Surveillance System, National Nosocomial Infections Surveillance (NNIS) System Report, data summary from Jan. 1992 through Jun. 2004, issued Oct. 2004, Am. J. Infect. Control., 32(8):470-85 (2004).
Newman et al., Motions of a Magnetic Particle in a Viscous Medium, J. Appl. Phys., 39:5566-5569 (1968).
Nie et al., Probing Single Molecules and Single Nanoparticles by Surface-Enhanced Raman Scattering, Science, 275(5303):1102-1106 (1997).
Noskin et al., National trends in *Staphylococcus aureus* infection rates: impact on economic burden and mortality over a 6-year period (1998-2003), Clin. Infect. Dis., 45(9):1132-40 (2007).
Nozawa et al., Smart Control of Monodisperse Stöber Silica Particles: Effect of Reactant Addition Rate on Growth Process, Langmuir, 21 :1516-1523 (2005).
Olsvik et al., Magnetic Separation Techniques in Diagnostic Microbiology, Clinical Microbiology Reviews, 7:43-54 (1994).
Paul et al., Stochastic Dynamics of Nanoscale Mechanical Oscillators Immersed in a Viscous Fluid, Phys. Rev. Lett., 92:235501-1-235501-4 (2004).
Petkus et al., Detection of FITC-Cortisol via Modulated Supraparticle Lighthouses, Anal. Chem., 78:1405-1411 (2006).
Puig-de-Morales et al., Measurement of Cell Microrheology by Magnetic Twisting Cytometry with Frequency Domain Demodulation, J. Appl. Physiol., 91:1152-1159 (2001).
Purcell et al., Life at Low Reynolds Number, Am. J. Phys., 45:3-11 (1977).
Richards-Kortum et al., Quantitative Optical Spectroscopy for Tissue Diagnosis, Annual Review of Physical Chemistry, 47:555-606 (1996).

(56) References Cited

OTHER PUBLICATIONS

Rife et al., Design and Performance of GMR Sensors for the Detection of Magnetic Microbeads in Biosensors, Sensors and Actuators A., 107:209-218 (2003).
Sakoulas et al., Relationship of MIC and bactericidal activity to efficacy of vancomycin for treatment of methicillin-resistant *Staphylococcus aureus* bacteremia, J. Clin. Microbiol., 42(6):2398-402 (2004).
Shankar et al., Experimental Determination of the Kinematic Viscosity of Glycerol-Water Mixtures, Proc. R. Soc. Lond. A., 444:573-581 (1994).
Shelton et al., Nonlinear Motion of Optically Torqued Nanorods, Phys. Rev. E., 71:036204-1-036204-8 (2005).
Shen et al., In situ Detection of Single Micron-Sized Magnetic Beads using Magnetic Tunnel Junction Sensors, Appl. Phys. Letts., 86:253901-1-253901-3 (2005).
Shine et al., The Rotation of a Suspended Axisymmetric Ellipsoid in a Magnetic Field, Rheol. Acta, 26:152-161 (1987).
Spellberg et al., Trends in antimicrobial drug development: implications for the future, Clin. Infect. Dis., 38(9):1279-86 (2004).
Stober et al., Controlled Growth of Monodisperse Silica Spheres in the Micron Size Range, J. Coll. Interface Sci., 26:62-69 (1968).
Su et al., A self-assembled monolayer-based piezoelectric immunosensor for rapid detection of *Escherichia coli* O157:H7, Biosens. Bioelectron., 19(6):563-74 (2004).
Talbot et al., Bad bugs need drugs: an update on the development pipeline from the Antimicrobial Availability Task Force of the Infectious Diseases Society of America, Clin. Infect. Dis., 42(5):657-68 (2006).
Taylor et al., Real-time molecular and cellular analysis: the new frontier of drug discovery, Current Opinion in Biotechnology, 12(1):75-81 (2001).
Tenover et al., The challenges of emerging infectious diseases. Development and spread of multiply-resistant bacterial pathogens, JAMA, 275(4):300-4 (1996).
Tiemersma et al., Methicillin-resistant *Staphylococcus aureus* in Europe, 1999-2002, Emerg. Infect. dis., 10(9):1627-34 (2004).
Valberg et al., Magnetic particle motions within living cells. Physical theory and techniques, Biophysical Journal, 52(4):537-550 (1987).
Varshney, Interdigitated array microelectrodes based impedance biosensors for detection of bacterial cells, Biosens. Bioelectron., 24(10):2951-60 (2009).
Verbridge et al., High Quality Factor Resonance at Room Temperature with Nanostrings Under High Tensile Stress, J. Appl. Phys., 99:124304-1-124304-8 (2006).
Vignola et al., Effect of Viscous Loss on Mechanical Resonators Designed for Mass Detection, Appl. Phys. Lett., 88:041921-1-041921-3 (2006).
Wagnieres et al., In vivo fluorescence spectroscopy and imaging for oncological applications, Photochemistry and Photobiology, 68(5):603-632 (1998).
Waigh, Microrheology of Complex Fluids, Rep. Prog. Phys., 68:685-742 (2005).
Witte et al., Changing pattern of antibiotic resistance in methicillin-resistant *Staphylococcus aureus* from German hospitals, Infect. Control Hosp. Epidemiol., 22(11):683-6 (2001).
Witte, Antibiotic resistance in gram-positive bacteria: epidemiological aspects, J. Antimicrob. Chemother., 44 Suppl A:1-9 (1999).
Yamazaki et al., Three-Dimensional Analysis of Swimming Properties of a Spiral-Type Magnetic Micro-Machine, Sensors and Actuators A., 105:103-108 (2003).
Yang et al., Interdigitated Array microelectrode-based electrochemical impedance immunosensor for detection of *Escherichia coli* O157:H7, Anal. Chem., 76(4):1107-13 (2004).
Zhao et al., A Rapid Bioassay for Single Bacterial Cell Quantitation Using Bioconjugated Nanoparticles, PNAS, 101:15027-15032 (2004).

\* cited by examiner

Magnetic Only

| Key: | Ⓑ Buoyant beads | Ⓜ Magnetic beads | ✛ Target analyte |
|---|---|---|---|
| | ⎯ Nontarget analyte | [N S] Magnet | |

| Mix magnetic and buoyant beads with analyte | - Perform magnetic separation<br>- Remove unbound analyte and unbound buoyant beads | - Remaining sample contains only magnetic objects, including those that are buoyant |
|---|---|---|

Buoyant Only

| Key: | Ⓑ Buoyant beads | Ⓜ Magnetic beads | ✚ Target analyte |
|---|---|---|---|
| | ⬌ Nontarget analyte | [N S] Magnet | |

Mix magnetic and buoyant beads with analyte

- Perform buoyant separation
- Remove unbound analyte and unbound magnetic beads

- Remaining sample contains only buoyant objects, including those that are magnetic

Magnetic and Buoyant Separation
Key:
- Ⓑ Buoyant beads
- Ⓜ Magnetic beads
- ✚ Target analyte
- ▭ Nontarget analyte
- [N S] Magnet
| Mix magnetic beads With analyte | - Perform magnetic separation<br>- Remove unbound analyte | - Add Buoyant beads<br>- Perform magnetic separation to buoyant beads | Only magnetic buoyant complexes remain complexes |
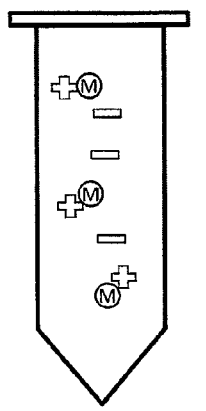
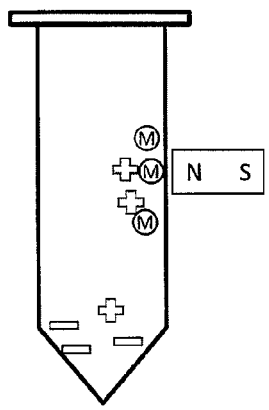
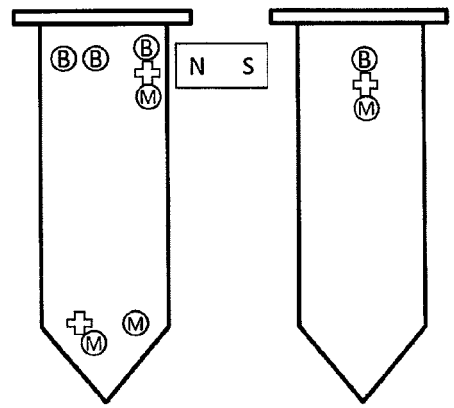
FIG. 4A     FIG. 4B     FIG. 4C     FIG. 4D

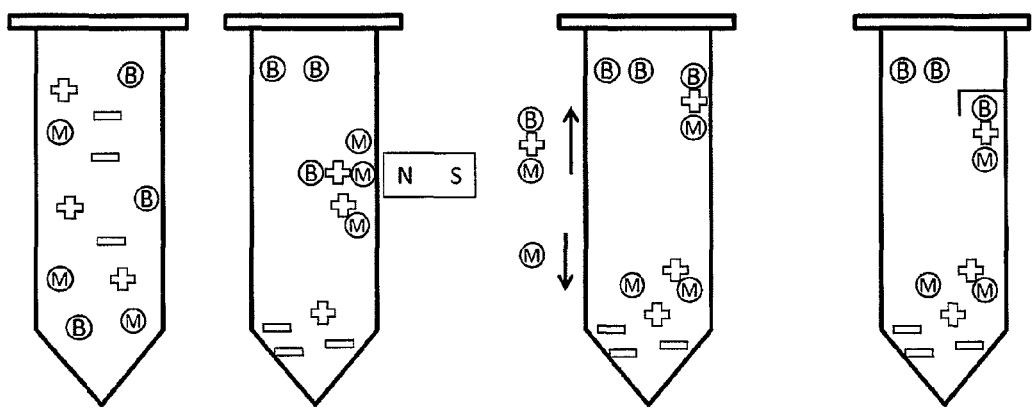

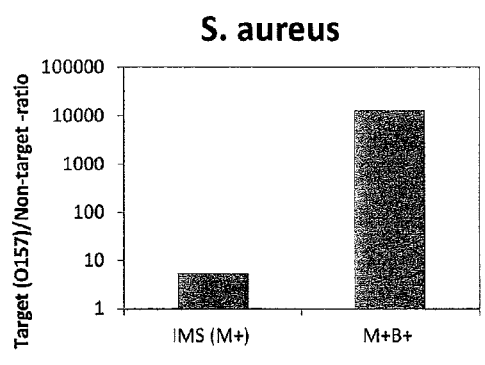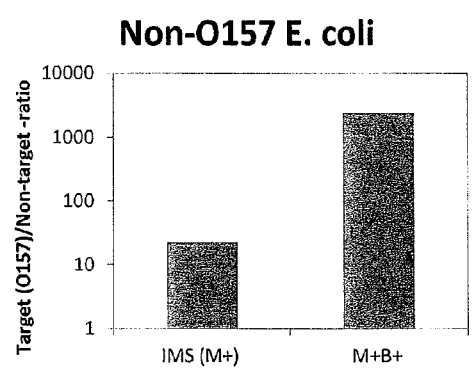
FIG. 6A
FIG. 6B

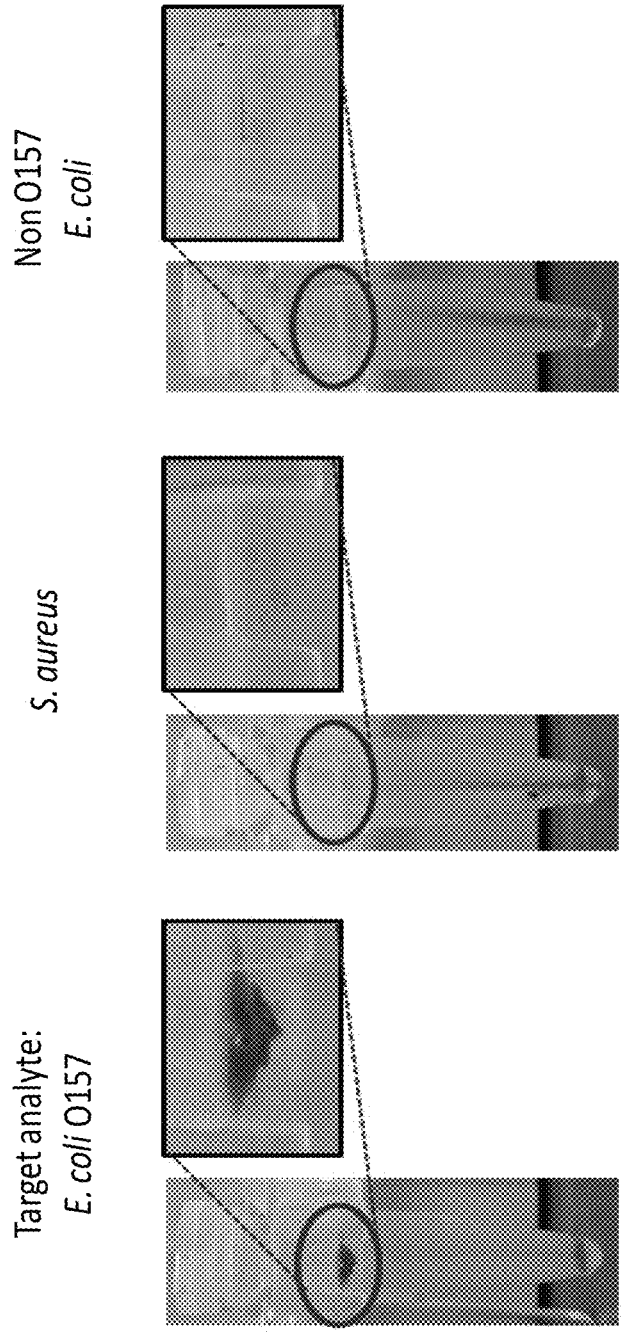

Key: Ⓑ Buoyant beads  Ⓜ Magnetic beads  ✚ Target analyte
▭ Nontarget analyte  [N S] Magnet Mix magnetic and buoyant beads with analyte Apply magnet gradient and let buoyant particles rise

- Bend tube and remove top fluid, removing buoyant
- Remove Magnet

- Straighten tube
- Only complexes float to top
- Visualize and/or remove complexes

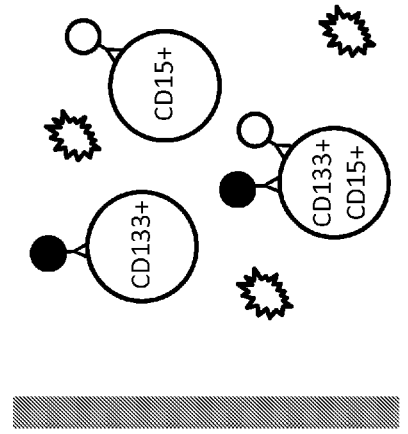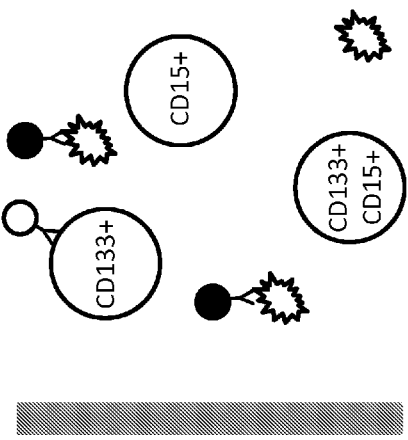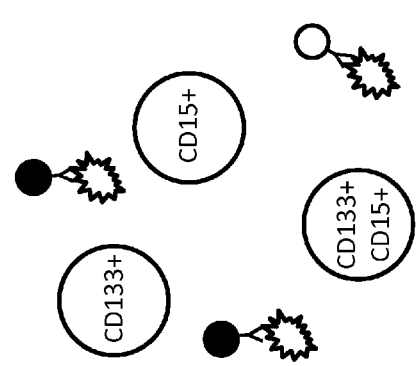
Fig. 21

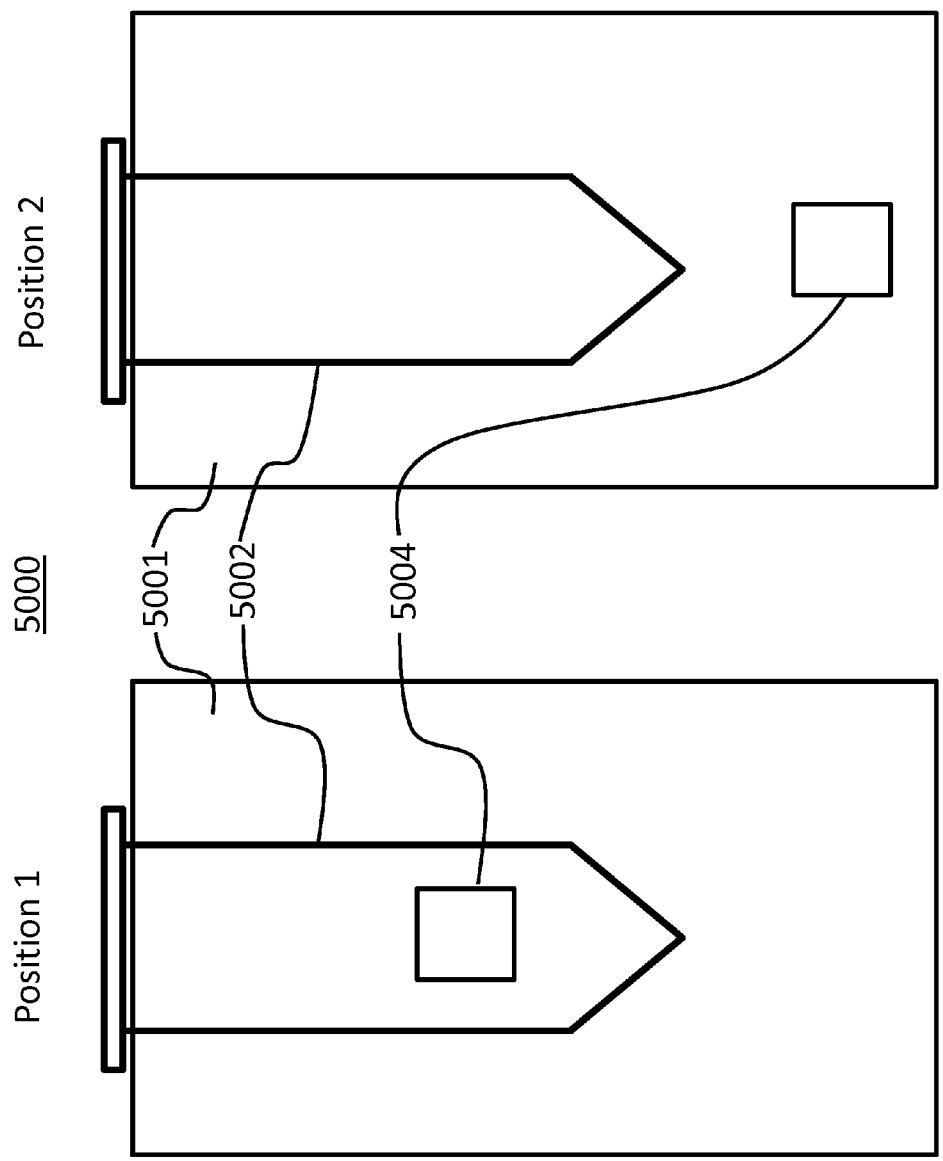

MULTI-MODE SEPARATION FOR TARGET DETECTION

CROSS REFERENCE TO RELATED APPLICATIONS

The present application claims the benefit of U.S. Provisional Application No. 61/642,305, entitled "Highly Specific Sandwich Separation and Standard Well Plate Operation for Analyte Detection and Cell Growth Monitoring," filed on May 3, 2012, which is hereby incorporated by reference in its entirety.

FIELD OF THE INVENTION

Described herein are methods, systems, reagents and devices for performing separation using two physical processes and for measuring and/or characterizing a target using asynchronous magnetic bead rotation on a solid interface.

BACKGROUND OF THE INVENTION

In the last thirty or so years, there have been dramatic changes in both sample preparation and testing procedures for numerous applications, including immunoassays, molecular diagnostics, medical microbiology, cell-based assays, and more. Inherent in many of these practical applications are some type of target isolation or separation and some type of target detection method. Improvements in specificity or time-to-results of these tests have come through either improvements in the sample preparation (e.g. isolation or separation of target) or improvements in the detection technologies.

One separation method, namely magnetic separation, has become ubiquitous in the application of isolating targets out of a fluidic sample. These targets range from specific whole cell pathogens, like bacteria, to nonspecific targets, like nucleic acids. A limitation that magnetic separation faces is that the specificity of the separation is governed by the specificity of a single antibody or other bead coating. This limitation stems from the fact that magnetic separation uses a single mechanism (i.e. magnetic forces) to separate the beads with bound target from the rest of the sample. Therefore, it leads to limited specificity and also to a high chance of non-specific binding. This is not only because of the single antibody or bead coating, but because of the sheer number of beads that make it through the process, each of which may have an adherent non-target. The number of magnetic particles in a separation process can be three or four orders of magnitude higher than the number of targets. This can result in non-targets being captured, which can affect methods like cell culturing or PCR, where non-targets can cause false positives or inhibit reactions. In applications like food testing, this limited specificity leads to the need of culturing captured cells on selective or colorimetric growth conditions to indicate a positive identification of the organism. Also in food testing, the presence of inhibiting agents binding to magnetic beads may limit the amount of initial sample that can be used for a PCR reaction.

Furthermore, because performing separation on a single physical mechanism allows for specificity from only a single biomolecule or coating (i.e. a single antibody), existing separation methods are not being used as visual assays. If separation could be used as a visual assay to indicate the presence of a target, there could be improvements in sensitivity and ease of use. However, in order to make the test accurate and practical, this would require the use of double specificity (i.e. like is done with a sandwich immunoassay) during the separation process. This may also require the ability to separate the sample using two different and distinct physical properties (i.e. magnetism in addition to another mechanism).

Lateral flow assays are one of the most common forms of visual assays and they often utilize some form of sandwich immunoassay. However, lateral flow assays also have limitations in both the amount of sample that can be used (for example 100 µL) and the resulting sensitivity of the method. Also, the line that indicates the presence of a target can be difficult to read. Finally, lateral flow assays are one of the few methods that can be performed as a one-step assay; however, they don't necessarily utilize magnetic separation and the advantages that separation provides, including the ability to use larger initial amounts of sample.

Once sample preparation—possibly using magnetic separation—has been completed, many downstream methods exist to detect the presence of the target or if the target is a cell, to measure its growth. These methods may include immunoassays, selective culturing, nucleic-acid techniques, or asynchronous magnetic bead rotation (AMBR). While these detection and culturing methods can all be improved by having better sample separation, there are also improvements that can be made specifically for AMBR.

SUMMARY OF THE INVENTION

Magnetic separation traditionally only utilizes the surface coating of a single type (for example the specificity of a single antibody). However, through the use of a differently labeled buoyant microspheres (for example antibody, protein, or nucleic acid labeled), as described herein, a sandwich complex can be formed that allows for a secondary physical separation to be performed in addition to magnetic separation. This secondary physical separation, herein called "two-bead separation," provides an additional level of specificity through formation of sandwich complexes. These complexes can then be used in various downstream methods, such as nucleic acid testing, cell-based assays, immunoassay detection, asynchronous magnetic bead rotation, or any other detection method that may benefit from highly specific separation.

The present application describes various techniques for two-bead separation as well as devices to perform two-bead separation.

The two-bead separation techniques described herein allow for increased specificity though use of surface coatings on two different types of beads. This may include antibodies, proteins, and nucleic acids (for example in hybridization assays), etc. The techniques allow for the efficient removal of "empty beads," which can occur, for example, where only targets having two specific different types of beads attached will make it through to the end of the separation process. The techniques also allow for proper visualization of the two bead complexes. When enough target is present, the two bead complexes can be visualized based on the physical properties of the two-different types of beads.

In this application, the term "two-bead" is used to refer to entities that include a target (e.g., cell, protein, antibody, nucleic acid, particle etc) with two different types of beads attached thereto. For example and without limitation, in some embodiments a target is associated with a plurality of magnetic beads and a plurality of buoyant beads, wherein the ratio of magnetic beads to buoyant beads confers overall magnetic and buoyant properties on the target to facilitate its isolation from a non-target.

Thus, two-bead separation allows for physical isolation and concentration on the basis of two distinct mechanisms: buoyancy and magnetism, which is not possible by methods that depend only on one mechanism of separation (i.e., only buoyancy or only magnetism). Only beads linked via a target make it through the two-bead separation process, minimizing the presence of beads without any attached target (e.g. "empty beads") and also providing increased specificity. Due to the dual nature of a two-bead complex (that is, they are both magnetic and buoyant), sandwiches (e.g., "two-bead" sandwiches) can be manipulated away from non-sandwich complexes (which are either magnetic, buoyant, or neither). Beads can be coated with a variety of moieties, including charge, nucleic acids, proteins, antibodies, etc. Also, there may be uses for coating the magnetic beads with a different moiety than what is coated on the buoyant beads. For example, magnetic beads could be used for depletion of one cell type ("negative separation"), while buoyant beads are used to capture the desired cells (e.g. "positive separation").

At the end of the separation process, any non-targets, magnetic beads not in a two-bead complex, and buoyant beads not in a two-bead will be separated out. All that remains is the sandwich complexes with the attached target. This is significant because, for example, if only 100 cells are attached to beads and $10^6$ beads are used in the initial binding procedure, only the beads with attached target will remain, reducing the number of "empty" particles by a factor of 10,000; therefore, also similarly reducing the potential for nonspecific bound targets to make it through the separation process. This may be advantageous for imaging or detecting the captured target that might have otherwise been difficult or impossible to image—this is due to the sheer presence of $10^6$ beads, each of which may be much larger than the target. It is well known that with enough magnetic beads in a sample, the presence of the beads can block light from a microscope or other optical or non-optical measurement method, making imaging or detection difficult.

This two-bead separation process could also be useful for a variety of applications that require sample preparation with high specificity, as is common in medical diagnostic, life science research, industrial food testing, and industrial water testing. Furthermore, the presence of the two-bead complexes can be visually confirmed, due to their unique location, resulting from the dual property of being both magnetic and buoyant.

Typically, techniques like lateral flow assays require use of a small amount of test sample with volumes on the order of 100 µL. However, using the magnetic-buoyant separation techniques described herein, one can use as much sample as is required to enable a visual confirmation of the presence of the two-bead formations. Tests described herein have been performed with as much as 10 mL of test sample at a concentration of $5\times10^4$ cfu/mL. The resulting complexes have been visualized. The advantage of using more sample is that the test sensitivity can be improved. Also, described herein are visual results (visible to naked eye) down to $5\times10^4$ cfu/mL of target organism.

Further improvement in sensitivity may be achieved through the use of more beads, beads of different sizes, longer binding time, optimized protocols, and/or use of larger sample volumes. In other examples, sensitivity may be increased by combining or implementing the present techniques with instruments to detect the presence of the magnetic-buoyant complexes, such as imaging, fluorescence, or magnetic bead detection instruments.

Also, the two-bead complex acts as an excellent sample preparation method for performing measurements, including for asynchronous magnetic bead rotation. The reason is that only the beads with attached target make it through the double separation process. This can result in many methods being more sensitive and enabling faster time to results.

For performing downstream analysis after two-bead separation, the buoyant particle and the magnetic bead can be removed from the target of interest. This can be done, for example, by linking an antibody via a modified biotin to the buoyant bead. In the presence of regular biotin, this modified biotin will be out-competed so that the cell is released from the buoyant bead. This will result in having only magnetic beads with attached cells and at the end of the process, there will only be targeted cells and only the beads with attached targets/cells. By use of elution, both beads can be removed, leaving only the target, or the magnetic bead can be removed. Alternatively, only the buoyant bead or only the magnetic bead can be selectively released. This may be advantageous for bringing one bead type with the attached target to a location of interest, such as the top of a droplet for buoyant or at the side of a vial for magnetic.

Thus the application also describes techniques for performing simultaneous separation (i.e., simultaneous two-bead separation) as well as single bead separation in a staged manner. For example, a two-bead separation process may include performing buoyant separation followed by magnetic separation, performing magnetic separation followed by buoyant separation, as well as performing both separations at the same time.

The disclosure therefore provides, in one aspect, a method of isolating a complex comprising a target, a magnetic bead and a buoyant bead from a sample, the method comprising: (a) contacting the sample in a solution with (i) a population of magnetic beads, each magnetic bead comprising a moiety that can specifically associate with the target under appropriate conditions and (ii) a population of buoyant beads, each buoyant bead comprising a moiety that can specifically associate with the target under appropriate conditions, wherein contacting results in formation of the complex; and (b) isolating the complex based on the combined movement of the complex in a magnetic field and in a gravitational or centrifugal field.

The disclosure contemplates isolation of more than one target in a sample. Multiple parameters contribute to the ability to isolate more than one target in a sample. It will be understood that a plurality of magnetic beads and a plurality of buoyant beads may be used in various combinations to isolate one or more targets in a sample. In one non-limiting example, three targets are isolated from a sample; one target is isolated via two-bead isolation, one target is isolated solely by magnetic bead isolation and a third target is isolated solely by buoyant bead isolation.

In another non-limiting example, the size of the magnetic beads relative to the size of the buoyant beads affects the ability of each of the beads to recognize and bind to its target. Sizes of magnetic beads contemplated by the disclosure include those that are from about 10 nanometer to about 100 micrometer in diameter. Thus, in one non-limiting example, a plurality of populations of magnetic beads (e.g., M1, M2, M3, M4, etc.) and buoyant beads (e.g., B1, B2, B3, B4, etc.) are added to a sample, wherein each population of magnetic beads and each population of buoyant beads each comprise a moiety that can specifically associate with one or more targets (e.g., T1, T2, T3, T4, etc.). In some embodiments, the beads in M1 and the beads in B1 each comprise a moiety that can specifically associate with T1. In such embodiments, the beads in M1 must be of a size that allows the beads in B1 to associate with T1. Thus, the disclosure contemplates formation of multiple two-bead complexes in a sample to isolate multiple targets. The disclosure also contemplates that two-bead isolation may be combined with single-bead isolation(s) to isolate more than one target from a sample.

The target is another parameter to be considered. By way of example, in an embodiment wherein the target is a receptor on a cell, knowledge of the relative size of the cell compared to the size of the magnetic beads and/or the buoyant beads will provide information that can be used to estimate variables such as (i) how many target receptors are on the surface of the cell; (ii) whether the magnetic bead moiety and the buoyant bead moiety should be designed to associate with the same target or different targets on the surface of the cell; and (iii) whether the magnetic beads and the buoyant beads should be added to the sample comprising the target at the same time, or in a specific order based on parameters (i) and/or (ii).

Additional parameters useful in the practice of the methods of the disclosure include, but are not limited to; (a) the viscosity of the solution in which the isolation is being performed relative to the buoyancies of beads; (b) the cross sectional area of the bead:target assemblies; (c) the use of two or more populations of buoyant beads wherein the populations have different buoyancies relative to each other and (d) in view of the foregoing parameters, ensuring that, following complex formation, the overall buoyancy of the complex exceeds the negative buoyancy imparted by both the mass of the magnetic beads bound to the target and the mass of the target.

In one embodiment, the magnetic bead moiety and the buoyant bead moiety are different. In another embodiment, the magnetic bead and the buoyant bead are added to the sample sequentially, and in a further embodiment, the magnetic bead is added prior to addition of the buoyant bead.

In various embodiments, the disclosure contemplates that the magnetic bead moiety and/or the buoyant bead moiety is selected from the group consisting of a protein, a charge and a nucleic acid. In certain embodiments, the protein is an antibody.

In further embodiments of the disclosure, it is contemplated that the target is selected from the group consisting of a cell, a protein, a nucleic acid and a small molecule. In a specific embodiment, the nucleic acid is genomic DNA. In further embodiments, the cell is a eukaryotic cell or a prokaryotic cell.

Thus, in some embodiments, the target and the magnetic bead moiety are each a nucleic acid. In these embodiments, it is contemplated that the target nucleic acid and the nucleic acid moiety on the magnetic bead are sufficiently complementary to hybridize to each other under appropriate conditions.

In another embodiment, the magnetic bead and/or the buoyant bead are removed following isolation of the target.

The magnetic bead moiety and/or the buoyant bead moiety comprise, in various embodiments, a detectable label. Accordingly, the disclosure provides methods wherein complex formation is detected by a detectable change. Methods for visualizing the detectable change resulting from complex formation include any fluorescent detection method, including without limitation fluorescence microscopy, a microtiter plate reader or fluorescence-activated cell sorting (FACS). It will be understood that a detectable label contemplated by the disclosure includes any of the fluorophores known in the art as well as other detectable labels known in the art. For example, labels also include, but are not limited to, chemiluminescent molecules, radioactive labels, dyes, fluorescent molecules, phosphorescent molecules, as well as any marker which can be detected using spectroscopic means, i.e., those markers detectable using microscopy and cytometry.

In some embodiments, the methods of the disclosure further comprise removing the magnetic bead and/or the buoyant bead that is not associated with the target from the sample, and in further embodiments the disclosure further comprises removing the magnetic bead and/or the buoyant bead that is associated with the target from the sample.

The disclosure also provides embodiments wherein the method further comprises an additional buoyant bead comprising a moiety that can specifically associate with a target, wherein the buoyant bead and the additional buoyant bead have different buoyancies relative to each other.

In some embodiments, the movement in the magnetic field and the gravitational or centrifugal field are performed simultaneously, and in further embodiments the movement in the magnetic field and the gravitational or centrifugal field are performed separately. In some embodiments, therefore, the complex is subjected to the magnetic field prior to being subjected to the gravitational or centrifugal field.

In another aspect, the disclosure provides an apparatus comprising: an inlet; a separation chamber device coupled to receive a sample from the inlet at a sample flow rate, the sample within the separation chamber containing targets, magnetic beads having a moiety that can specifically associate with the targets under appropriate conditions, buoyant beads having a moiety that can specifically associate with the targets under appropriate conditions, and formed complexes comprising the target and one or more magnetic beads and one or more buoyant beads, the separation chamber having at least one outlet positioned to receive and isolate the formed complexes from a non-complex within the sample; a magnet movable relative to a portion of the separation chamber, movable from an adjacent to proximal position relative to the outlet, for affecting specificity of isolation of the formed complexes, the movement of the magnetic resulting in an adjustable magnetic force controllable to isolate the formed complexes based on the magnetic moment of the one or more magnetic beads associated with the targets and based on the buoyancy of the one or more buoyant beads associated with the targets.

In some embodiments, the separation chamber device comprises a plurality of separation chambers, in a sequential configuration, where each successive separation chamber provides further isolation of the formed complexes.

In various embodiments of the disclosure, it is contemplated that the separation chamber device is a vial, is rotatable, and/or is integrated with the inlet and outlet.

In another embodiment, the magnet is movable along a length of the separation chamber to adjust the position and isolation of the formed complexes. In a further embodiment, the magnet is a rotatable around the separation chamber, and in a still further embodiment the magnet is configured to produce a rotating magnetic field.

The disclosure also provides embodiments wherein the apparatus further comprises a visualization region for analyzing the formed complexes isolated within the separation chamber. In some embodiments, the visualization region is configured to allow illumination of the separation chamber using an external illumination source and detection of resulting emissions from the formed complexes using an external detector. In further embodiments, the visualization region is configured to allow illumination of the separation chamber using an integrated illumination source and detection of resulting emissions from the formed complexes using an integrated detector.

BRIEF DESCRIPTION OF THE DRAWINGS

FIGS. 4A, 4B, 4C, and 4D show the process of performing magnetic and buoyant separation to isolate magnetic-buoyant sandwich complexes.

FIGS. 5A, 5B, 5C, and 5D show an alternative way of performing magnetic and buoyant separation to isolate magnetic-buoyant sandwich complexes.

FIGS. 6A and 6B shows the results comparing magnetic separation only (M+) to magnetic-buoyant separation (M+B+) for ratios of E. coli O157 to both S. aureus and non-O157 E. coli.

FIGS. 8A, 8B, and 8C compare the visualized results within a vial for E. coli O157:H7 (target), S. aureus, and non-O157 E. coli.

FIG. 14A shows a magnetic bead group rotating on a solid interface, experiencing drag ($F_D$) and friction ($F_f$) forces. FIG. 14B depicts when bacteria grow and form colonies, they increase the distance between the bead group and interface, therefore decreasing the overall drag experienced by the group. This can be seen as a reduction in the rotational period (early time results of FIG. 14D). FIG. 14C shows that when bacteria grow to sufficiently high concentrations, the drag and friction forces increase, therefore slowing down the group rotation. FIG. 14D shows the rotational period over time for an AMBR sensor at a solid interface for the scenarios in FIGS. 14A, 14B, and 14C.

FIG. 21 illustrates three different types of two-bead separation processes, in accordance with an example.

FIG. 28 illustrates a separation chamber and magnet control configuration, in accordance with yet another example.

DETAILED DESCRIPTION OF THE INVENTION

In general, the reagents, methods, systems and devices described herein are directed toward the improvement of sample preparation and detection relating to two-bead separation or buoyant separation.

Two-Bead Separation and Detection

Figures 1A, 1B:
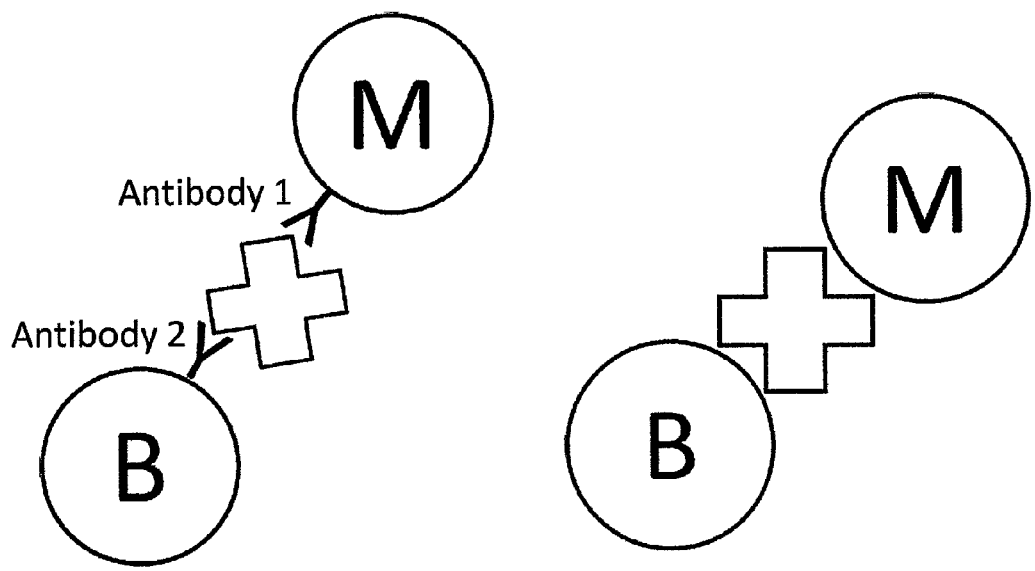
FIG. 1A shows an antibody complex that is used in the described sample.
FIG. 1B shows a sandwich complex, using a non-antibody approach, such as proteins, aptamers, non-specific binding, or other ways to make a sandwich.

A schematic representation of an idealized two-bead complex is shown in FIG. 1. FIG. 1A shows a sandwich complex formation of a magnetic bead coated with an antibody specific to the target of interest, the target, and a buoyant bead coated with a different antibody that is specific to the target of interest. As an alternative, FIG. 1B schematically illustrates a two-bead complex formed through other ways, such as coated beads with proteins, aptamers, nucleic acids, charges, or other coatings. Furthermore, each target may have a plurality of magnetic and buoyant beads.

Figure 2A:
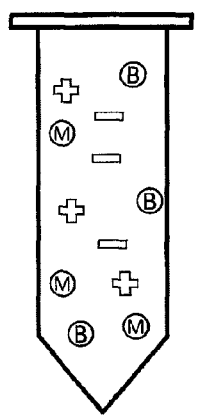
FIGS. 2A, 2B, and 2C show the process of performing magnetic separation only.
Figure 2B:
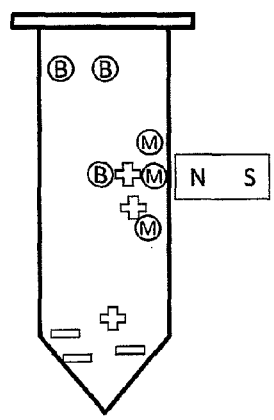
Figure 2C:
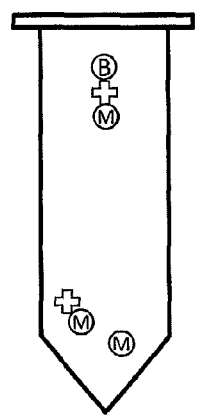

Traditionally, when magnetic separation, similar to the shown in FIG. 2, is used for magnetic separation, affinity magnetic separation, or magnetic-activated cell sorting, only the specificity of a single antibody/ligand can be taken advantage of. Often magnetic separation is used to capture a target of interest, where the target can be a bacterial cell, a mammalian cell, a protein, a nucleic acid, etc. Due to the limited specificity of the single antibody/ligand coated on to the surface of the beads, the separation process depends on detection methods to add additional specificity, such as cell staining, growing cells in selective media, performing lateral flow assays, or performing nucleic acid testing. If buoyant particles, as shown in FIG. 2A, are introduced into the sample, the magnetic separation process can still be followed. This is shown in FIG. 2B, where a magnet is applied to the side of the vial to separate non-magnetic from magnetic entities. However, since some sandwich complexes will form between the magnetic and buoyant particles, there will be two populations left at the end of the process: those that are magnetic and buoyant and those that are only magnetic (shown in FIG. 2C). Example beads used for magnetic separation include MACS microbeads (Miltenyi Biotech), Dynabeads (Life Technologies), EasySep (StemCell Technologies).

Figure 3A:
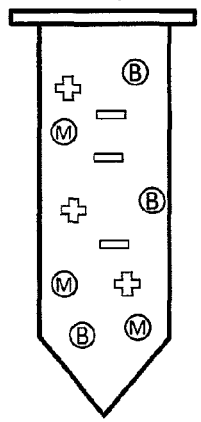
FIGS. 3A, 3B, and 3C show the process of performing buoyant separation only.
Figure 3B:
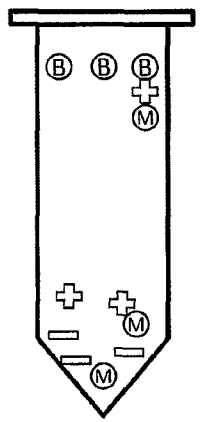
Figure 3C:
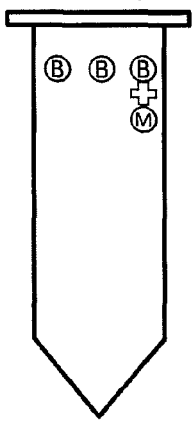

The present techniques also use buoyancy to accomplish separation. As described herein, buoyant separation can be used in a manner similar to magnetic separation, through the use of a single antibody/ligand, which can lead to non-specific binding. If magnetic particles, as shown in FIG. 3A, are introduce into the sample, a buoyant separation process may still be followed. This is shown in FIG. 3B, where the vial is placed in a centrifuge or left in earth's gravitation field to allow for sedimentation and buoyancy to take place. The non-buoyant pellet can then be removed (alternatively the buoyant layer of beads at the top of the vial can also be removed with a pipette tip). However, since some sandwich complexes will form between the magnetic and buoyant particles, there will be two populations left at the end of the process, namely those that are magnetic and buoyant and those that are only magnetic, which is shown in FIG. 3C. Example products used for buoyant separation include Ficoll gradient. Some beads that are both magnetic and buoyant called, Ferrospheres-N beads, have been offered by Microsphere Technology Ltd. of Adare, Ireland. But while such combined function beads may be implemented in the present techniques, generally speaking, they do not provide the separate individual advantages of performing buoyant and magnetic separation as is taught in the present application.

When magnetic and buoyant particles are used as described herein, there can be two populations of beads at the end of buoyant or magnetic separation. Either process has a major limitation because non-specific binding can still take place on the non-sandwich complex beads and the process does not eliminate the beads that do not have any bound target. Furthermore, each process fails to specifically isolate the two-bead complexes that are formed when using buoyant and magnetic beads. Indeed, one beneficial feature of the described invention is to have a process that results in a single population of beads, namely the magnetic-buoyant sandwich complexes that is shown in FIG. 1A (or alternatively FIG. 1B).

There are several examples of how to accomplish this. One example is shown in FIG. 4. First, a sample is mixed with magnetic beads. After allowing the beads to bind to the target, shown in FIG. 4A, magnetic separation can be performed, which is shown in FIG. 4B. This leaves only magnetic beads with bound target. To this sample, buoyant beads are added and binding is allowed to occur (with mixing). This will result in the formation of two-bead complexes. Then a magnet can be applied to the buoyant part of the sample, either by use of a short range external magnet, shown in FIG. 4C, or by immersing a short range magnet with a protective sheath into the buoyant layer. This allows for removal of all particles that are not both magnetic and buoyant, leaving only magnetic-buoyant sandwiches as shown in FIG. 4D.

An example procedure of what is depicted in FIG. 4 is as follows:
First, 1 mL of appropriately diluted bacteria (*E. coli* O157: H7 (ATCC 35150), non-O157 *E. coli* (ATCC 25922), or *S. aureus* (ATCC 29213)) is mixed with 20 μL of anti-*E. coli* O157 antibody-coated magnetic beads (Invitrogen #710-03). Beads and cells are allowed to bind for 10 min at 37 deg C. Magnetic separation is performed 3 times with a 5 second vortex at 3000 rpm between each step. At this point in the process, samples are appropriately diluted and plated to allow for the colonies to be counted the following day (these are labeled as "M+" or only magnetic separation). Next, 100 μL of 10 μm, anti-*E. coli* O157 coated buoyant silica beads are added to the samples. The samples are incubated at 37 deg C. with 60 rpm end-over-end rotation for 15 minutes to allow sandwich complexes to form. The samples are then centrifuged for 2 minutes at 400×g. This is followed by performing magnetic separation (with a PickPen, Cat #23001, Sunrise Science Products, Inc.) to only the buoyant particles. The pellet on the PickPen is captured and released into CA-MHB three times before finally being resuspended into CA-MHB. Samples were then diluted and plated so that the colonies could be counted the following day (these are labeled as M+B+, which stands for magnetic and buoyant separation). The comparison of M+ and M+B+ plate counts can be seen in FIGS. 6 and 7.

Alternatively, magnetic and buoyant beads can be introduced simultaneously to the sample as the first step, allowing for a one-step or near one-step detection process and a simplified separation process. This other example method that can be used to separate out only magnetic-buoyant complexes is shown in FIG. 5. First, a sample is mixed with magnetic and buoyant beads. After allowing the beads to bind to the target, shown in FIG. 5A, magnetic separation can be performed, which is shown in FIG. 5B. The population of entities that are pulled to the wall of the vial, include magnetic beads without target, magnetic beads with target, and magnetic-buoyant complexes. Once the magnet is removed, the magnetic-buoyant complexes rise and the magnetic beads fall under gravitational forces, which shown in FIG. 5C. This step can be sped up by using a centrifuge, if needed. At this point, the magnetic-buoyant complexes may be visualized, which indicates the presence of the target, which itself is "detection event" and may have uses for various diagnostic purposes or may be used to indicate the separation process is working. Furthermore, a "catch" can be attached to the interior of a standard vial to keep the magnetic-buoyant particles from rising all the way to the top of the fluid, which is shown in FIG. 5D. This keeps the magnetic-buoyant complexes separate from the buoyant beads, which may allow for easier visualization and for easier recovery of the bound complexes.

An example procedure of what is depicted in FIG. 5 is as follows:

First, 1.0 mL of appropriately diluted bacteria (*E. coli* O157:H7 (ATCC 35150), non-O157 *E. coli* (ATCC 25922), or *S. aureus* (ATCC 29213)) is mixed with 20 μL of anti-*E. coli* O157 antibody-coated magnetic beads (Invitrogen #710-03), followed by 100 μL of 10 μm, anti-*E. coli* O157 coated buoyant silica beads. The samples are incubated at 37 deg C. with 60 rpm end-over-end rotation for 15 minutes to allow sandwich complexes to form. The vials are then placed into a magnetic separation rack for 2-3 minutes. After this, the vials are removed from the rack to allow for the magnetic beads to fall and the magnetic-buoyant complexes to rise. Custom vials were also made to catch or capture the magnetic-buoyant beads as shown in FIG. 5D and by making a triangular "bead catcher" (e.g. ledge) with the tip of the triangle pointing up (or toward the top of the vial). This general process is shown in the sequence of images of FIG. 9.

To demonstrate the improvement of two-bead separation over magnetic separation, the process described in FIG. 4 was followed and the culture plates for magnetic separation and two-bead separation described in herein were compared. These results are shown in FIG. 6. The bar graphs show the comparison of the ratio of target bacteria to non-target for standard magnetic separation (M+) and for sandwich separation (M+B+). The results are the average of three separate repetitions of the experiment. The results show a 100 to 1000 fold improvement over standard immunomagnetic separation. When using standard immunomagnetic separation (M+), both *S. aureus* and non-O157 *E. coli* had a ratio of target number of cells versus non-target number of cells of approximately 10. However, when sandwich separation (M+B+) was used, the corresponding ratios were approximately 100 times higher or more. In fact, in some cases, no *S. aureus* was found at the end of the M+B+ process, even when plating an entire vial of solution (~1 mL, where only 100 μL is usually plated). These results were obtained by comparing the number of bacteria at the end of each separation process and were performed with pure cultures. When comparing M+ separation to M+B+ separation, the efficiency of target capture fell from 40% to 2%; however, non-target *S. aureus* capture efficiency fell at the same time from 2% to <0.00003% and non-target *E. coli* from 1% to 0.001%.

Figure 7:
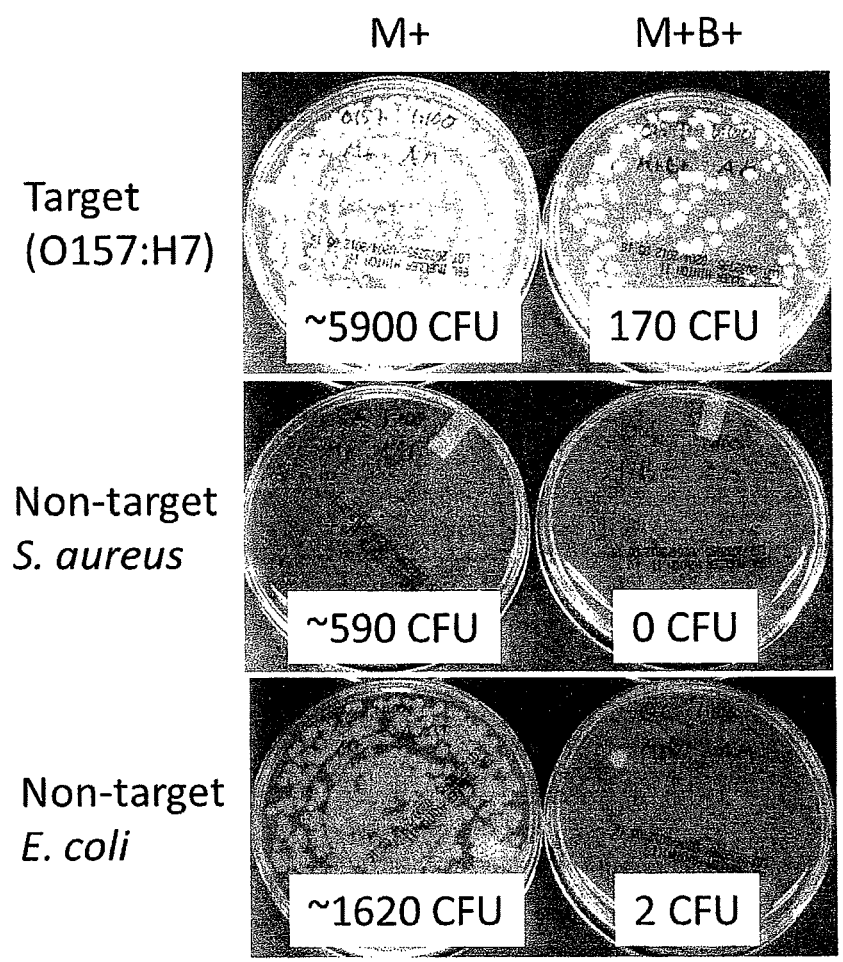
FIG. 7. shows a series of culture plates, comparing magnetic separation only (M+) to magnetic-buoyant separation (M+B+) for E. coli O157:H7 (the target cell), S. aureus, and non-O157 E. coli.

For comparison purposes, images were taken of the culture plates (1:100 dilutions) described herein, which is shown in FIG. 7. The pictures show plates after completing M+ and M+B+ separation processes. The shown cell counts were estimated from appropriately diluted plates (e.g. <300 cfu/plate). Again, for M+B+ of *S. aureus*, it can be seen that no cells were counted in this dilution. This is significant in comparison to M+ of *S. aureus*, where 590 cells were estimated. The target cell efficiency for M+B+ separation process is anticipated to improve once smaller buoyant and/or magnetic beads are used.

Not only can the magnetic-buoyant method act in a way that improves the specificity of separation, it can also be used to detect the presence of a target. FIG. 8 shows a comparison of vials for target and non-target cells. This figure shows that sandwich complexes specifically form in the presence of *E. coli* O157:H7 (at 107 cfu/mL), and not in the presence of non-O157 *E. coli* or *S. aureus* (at 108 cfu/mL). FIG. 8A shows the target cell (*E. coli* O157:H7) at a concentration of 107 cfu/mL. The presence of the target cells can be seen as the sandwich complexes form, which results in magnetic floating complex shown in FIG. 8A. FIGS. 8B and 8C show non-target cells (*S. aureus* and Non-O157 *E. coli*) at a concentration of 108 cfu/mL. In both of these cases, no magnetic-buoyant complexes can be visualized and from the counts herein, it is assumed that no sandwich complexes formed.

Figure 9A:
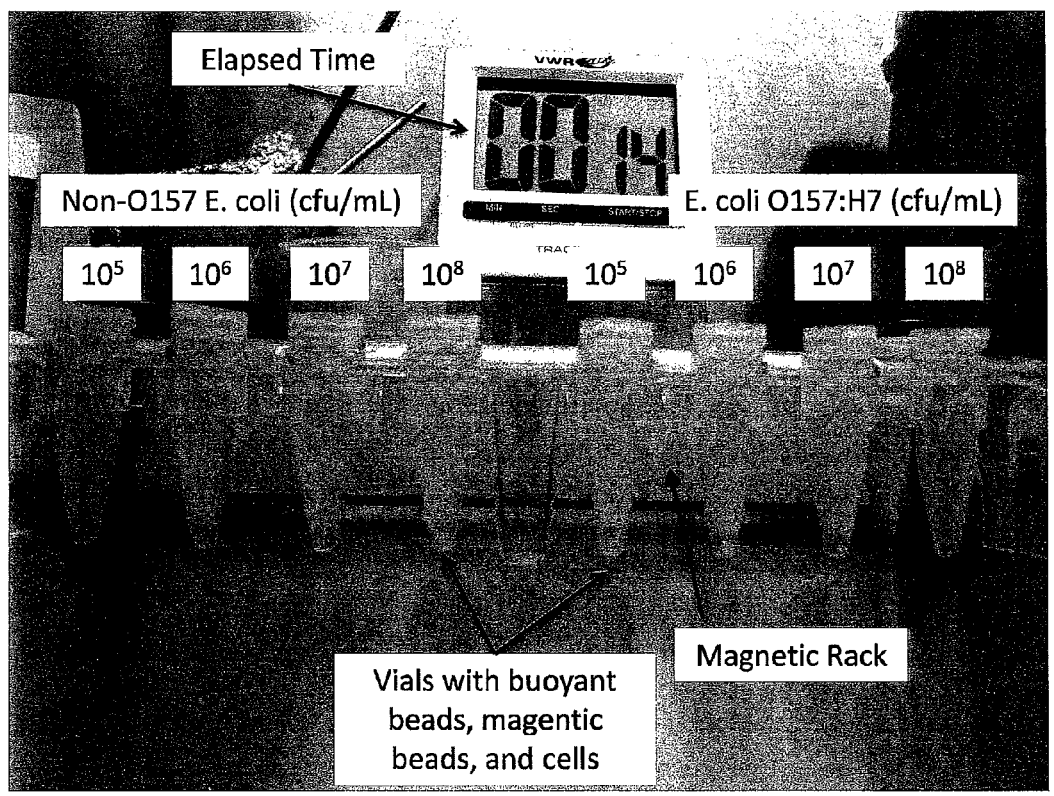
FIGS. 9A, 9B, 9C, 9D, and 9E show the process for performing magnetic and buoyant separation in series to visualize complexes.
Figure 9B:
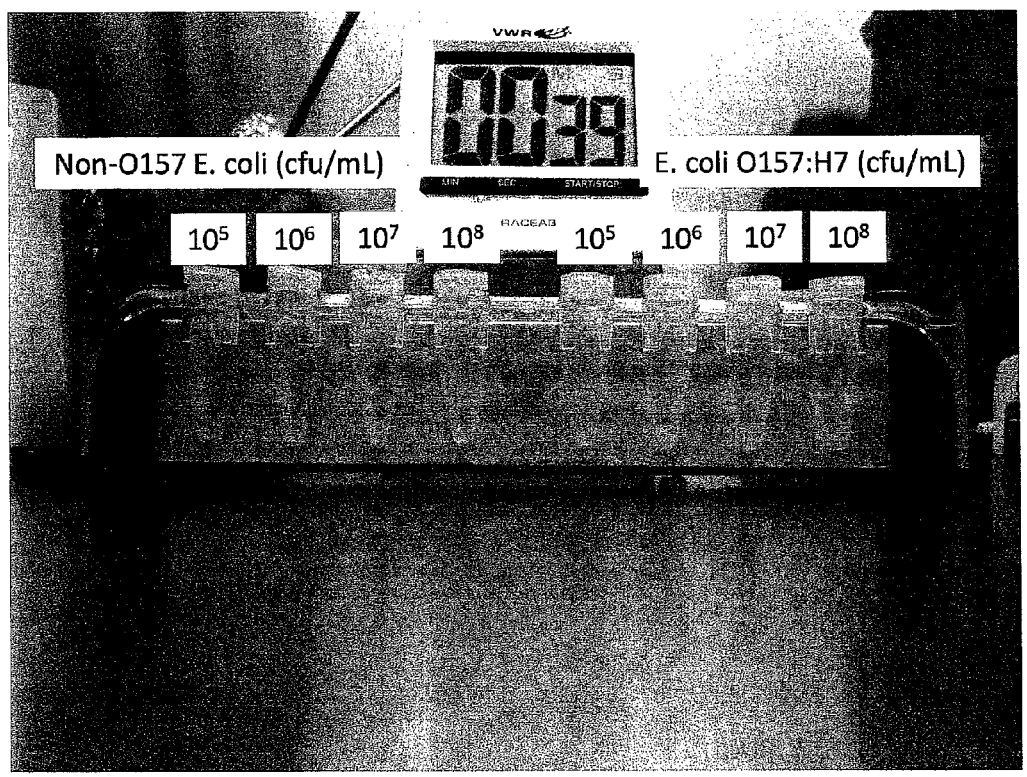
Figure 9C:
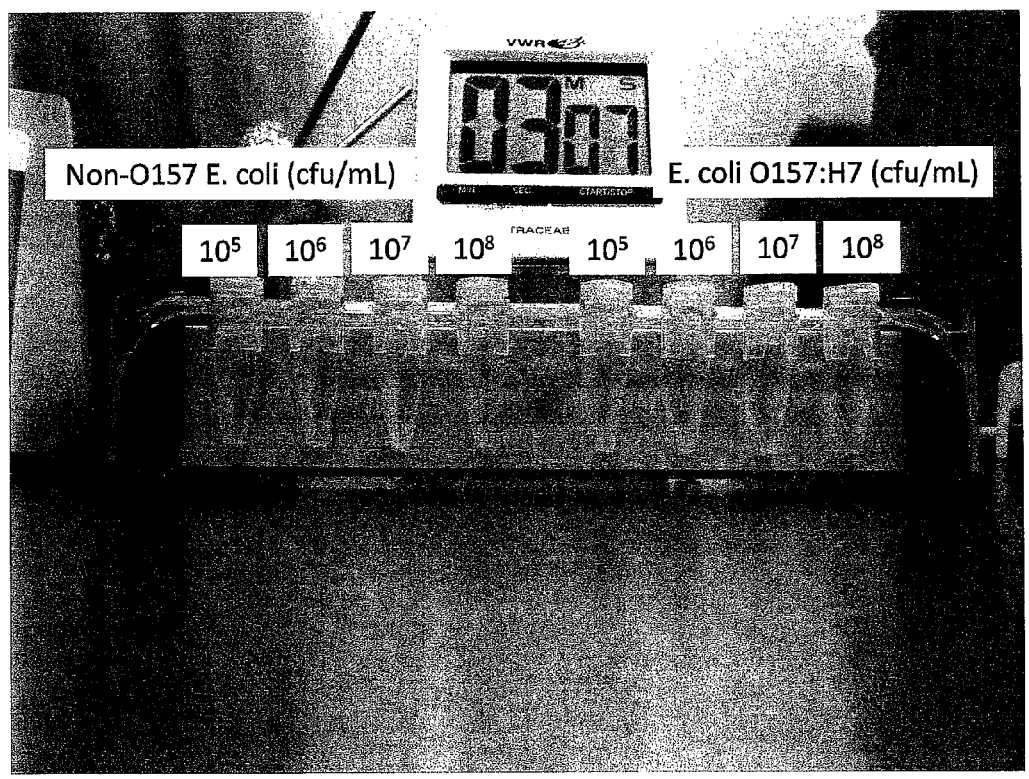
Figure 9D:
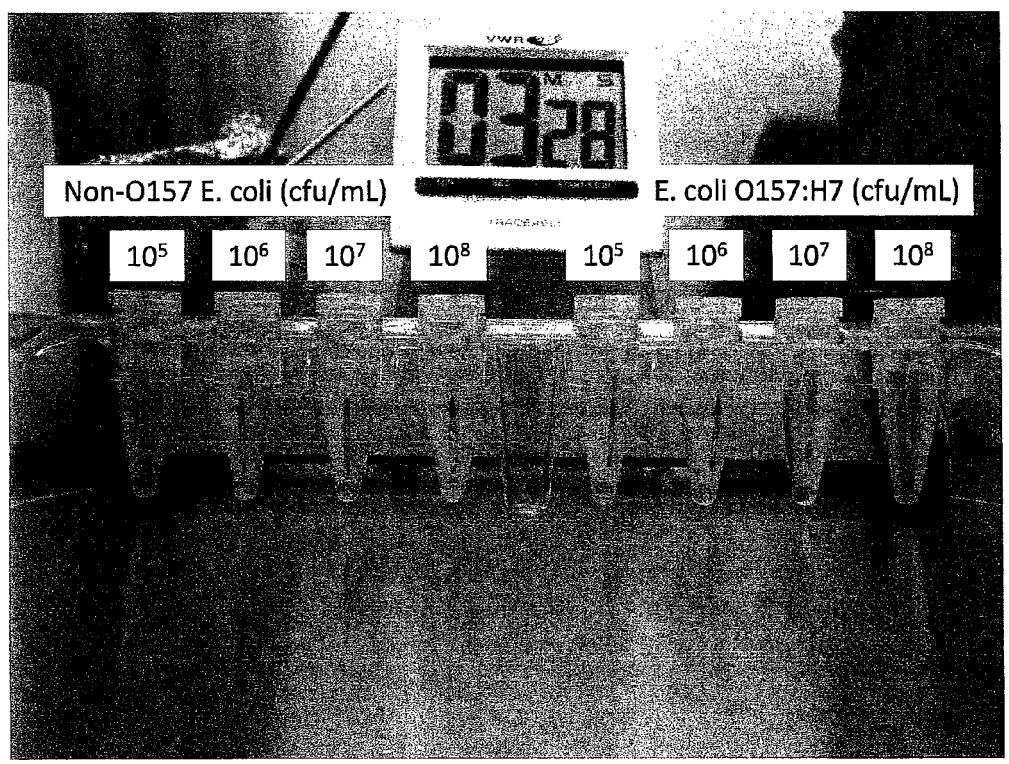
Figure 9E:
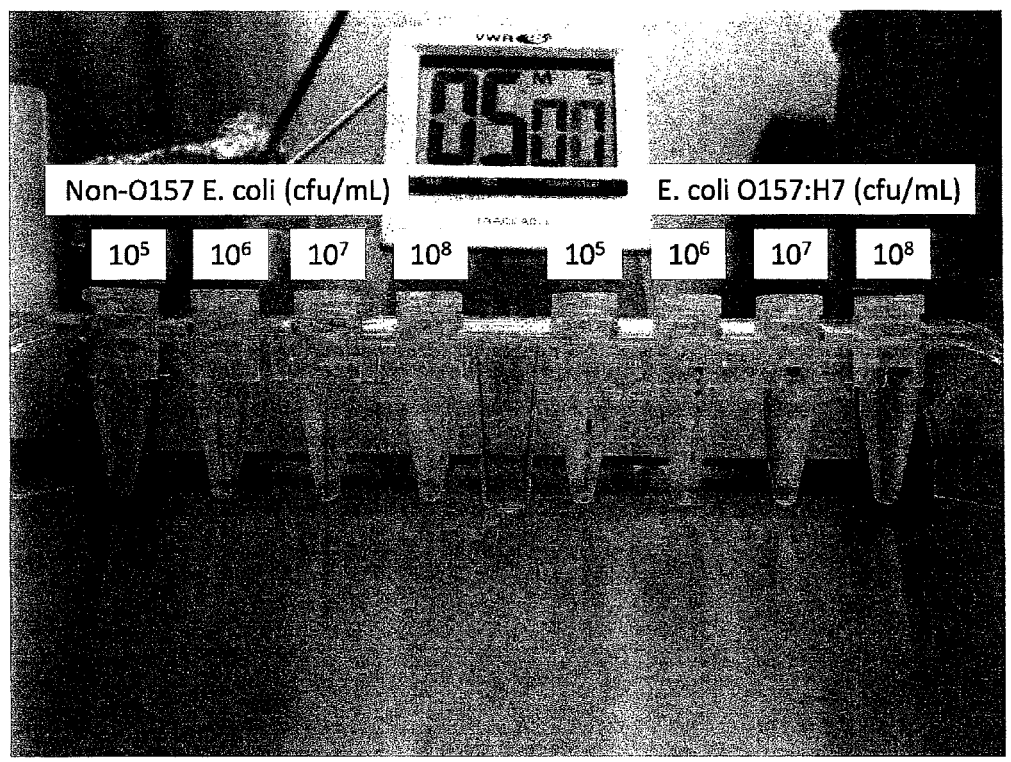
Figure 10A:
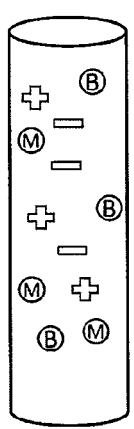
FIGS. 10A, 10B, 10C, and 10D illustrate the process of performing magnetic and buoyant separation in a tube, which allows for easy extraction of magnetic-buoyant complexes.
Figure 10B:
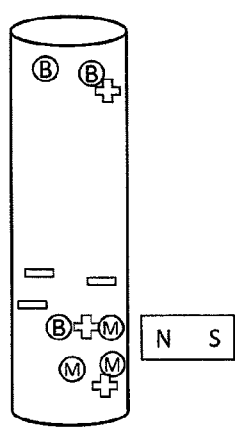
Figure 10C:
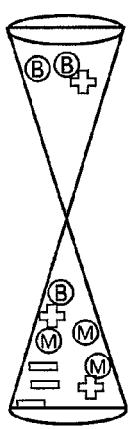
Figure 10D:
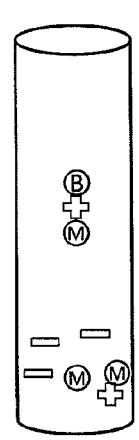

To demonstrate an example one-step protocol in accordance herein, the target cell (*E. coli* O157:H7) and non-O157 *E. coli* were compared at concentrations of $10^5$, $10^6$, $10^7$, and $10^8$ cfu/mL. After the sample was mixed with the magnetic and buoyant beads, the vials were placed in a plastic rack that fits over a magnetic rack. FIG. 9A shows the vials in the plastic rack before being placed on the magnetic rack. The shown elapsed time (after 15 minutes of binding) was 14 seconds. FIG. 9B shows the vials in the plastic rack, after being placed on the magnetic rack. The elapsed time was 39 seconds. FIG. 9C shows the vials in the same position as FIG. 9B, but with 3 minutes and 7 seconds of elapsed time. This is sufficient time for most magnetic bodies to be pulled to the side wall of the vial. There is an already obvious difference between target and non-target cells, which is evidenced by the size, shape, and color differences of the pellet formed on the interior of the vial. FIG. 9D shows the vials in the plastic rack, after being removed from the magnetic rack. Each vial was rotated 180 degrees, after being taken off of the rack, to allow for easier viewing of the pellets. Again the differences in the color, shape, and size of the pellets can be seen between target and non-target cells. The elapsed time was 3 minutes and 28 seconds. Finally, the beads were allowed to rise or fall, under gravitation forces, which is shown in FIG. 9E. After 5 minutes of total elapsed time, no non-target cell vials show any floating complexes; however, the target cell vials all have visible floating complex formation. The cell counts, performed the following day indicated that the lowest target concentration was $5 \times 10^4$ cfu/mL.

This procedure was also followed by using 10 mL of sample instead of 1 mL at $5 \times 10^4$ cfu/mL. The 10 mL sample produced a larger visible magnetic-buoyant complex. Again the sensitivity of this technique is high due to the ability to use a large amount of sample volume. This is potentially one large advantage over lateral flow assays, which often are limited in their use of sample volume. Furthermore, if performed properly, the magnetic-buoyant complexes may not fade over time.

If the sample shown in FIG. 9 is mixed intermittingly and cells grow or target concentration increases, the visualized magnetic-buoyant complex becomes larger and larger. This could be used to indicate cellular growth or increases of other targets of interest within the closed system.

As can be seen in FIG. 9, there is a concentration dependence of the visualization of the two-bead complexes. As a result, this could be used for quantitative immunoassays. Furthermore, this has been used to monitor growth of the target cell within the vial. Being able to monitor growth allows for also measuring the response of the cells to chemical agents, such as antimicrobials. From what this application teaches, one could design a test where one vial has 0 ug/mL of oxacillin and the other vial has a higher concentration of oxacillin so that it is at the CLSI-defined breakpoint that indicates resistance. With these vials the presence of the *S. aureus* (or other bacteria) could first be detected and then the growth could be monitored over a short time to determine if the bacteria are resistant or not.

Also, any of the procedures described so far can be combined with the step of elution, where the target cell can be released from both beads or selectively from just the magnetic bead or just the buoyant bead (alternatively the cells could be lysed while still attached to the beads). This is one reason why this sample preparation process is excellent for combination with various downstream methods, such as Mass Spectrometry, realtime PCR, cell culturing, sequencing, etc.

Another alternative separation process is shown in FIG. 10. This separation process uses flexible tubing that can be sealed at both ends. The tube can be bent or pinched to isolate buoyant from non-buoyant beads. FIG. 10A show the sample mixture, including magnetic beads, buoyant beads, target, and non-target. After sufficient time to bind, a magnet is applied to the lower part of the tubing, which is shown in FIG. 10B. The tube can then be pinched or bent so that the buoyant beads are isolated from the rest of the sample (shown in FIG. 10C). The buoyant beads can then be easily removed. After removal of the buoyant beads and removal of the magnet, the magnetic-buoyant beads will rise to the top of the tubing, which is shown in FIG. 10D. This allows for visualization of the remaining complex or for extraction. Further isolation can be performed by bending the tube again after the step shown in FIG. 10D. This would separate the magnetic-buoyant complexes from the rest of the sample.

Another separation process can be implemented within the tip of a pipette. This is significant due to the common used place of automated pipetting systems and liquid handling robots. For this separation method, a magnet may be place at the side of the pipette and the fluid is expelled. Next, the magnet may be removed and buoyancy allowed to take over further separation. This would be an example of sequential, multi-mode separation, where each separation type occurs individually or substantially individually. Then all but the top of the fluid in the pipette is expelled. This leaves only the two-bead complex in the pipette tip. This process could also be reversed so that the buoyant separation takes place first and is followed by magnetic separation.

Multiplexing may also be possible when using the magnetic-buoyant separation process. This is possible by using different colored floating spheres or magnetic labels to indicate the presence of different targets. Alternatively, if many different types of cells are captured, various colored antibodies or dyes may be used to multiplex. One embodiment includes constructing a device that detects these colors through fluorescent or imaging capability. This device can detect the two-bead complexes or buoyant beads at top of a drop and may include a component that provides excitation or illumination (laser, LED, etc), a detection component to measure intensity or color (photodetector, photomultiplier tube, ccd camera, etc.), optical components to support the redirection of the incoming, excitationing, illuminating, or fluorescent light (lenses, mirrors, filters, etc), a magnet. Multiplexing is also possible by adding and removing floating beads in a serial fashion. So each additional target test may take 15 minutes for each additional target detected.

The two-bead separation method may also be used for capturing rare cells, such as circulating tumor cells or bacteria in the blood. Since the method eliminates unbound beads, large amounts of magnetic and/or buoyant beads can be used for the initial capture, enabling more favorable binding kinetics. Because the two-bead separation method provides the ability to isolate beads that have cells and beads that do not, the number of beads may be reduced so much that the small amount of beads that have cells would be easy to image or detect using standard methods. As an example, when capturing 100 cells with 1,000,000 beads, when using the traditional IMS method, any detectable signal from the cells may be overwhelmed by the amount of magnetic particles in the final sample. Using the two-bead separation, only the fraction of magnetic beads that is sandwiched to a buoyant particle will remain in the final step, allowing the signal from the cells or targets to be detected. The two-bead method will also work well in raw specimen, such as blood to look for specific cells, including bacterial or cancerous cells. The method can be performed and the sandwich complexes visualized/detected while still in the raw specimen. This method may be low cost, simple, and sensitive. For blood testing of circulating tumor cells, the magnetic and buoyant beads may be coated with anti-epithelial antibodies.

Furthermore, for testing of rare cell or other targets, the benefit of the magnetic-buoyant method can be used to concentrate the final two-bead complexes to allow for simple detection or imaging of the resulting complexes, using more simplified visualization modes, such as a mobile phone, lower powered optics, low power microscope, etc.

Once magnetic and buoyant separation is completed, the complexes can be concentrated by either their buoyant properties or magnetic properties to a point location for detection. This is advantageous because no other standard separation technique allows for elimination of beads that do not have any bound target. If beads without target were present at the end of the process, imaging and detection of the rare targets/cells would be difficult if not impossible. This has been performed in a droplet system and in a standard 96 and 384 well plate. The well plate can then be placed within a plate reader to characterize results.

Also, after performing magnetic and buoyant separation, an additional level of specificity can be added. There are several ways to do this. One example is to culture the cells in selective media after the magnetic-buoyant separation process is completed. A second example is to add fluorescent antibodies or staining to the target of interest—again this is done after performing magnetic-buoyant separation. In both cases, the level of specificity can be very high because three levels of targeting can be used.

Theoretically, there is no lower limit for the number of cells that this method may be used to detect. This is why it may be especially useful for detecting rare cells or targets in the blood or other bodily fluids. Furthermore, there is no limit on the amount of fluid that can be used in the initial binding process, which allows for even higher sensitivity compared to methods for which this restriction applies, such as lateral flow assays.

In terms of visual detection of the magnetic-buoyant complexes, if it is assumed the human eye can discern a 200 um dot, this is equivalent to ~400 spheres with 10 μm diameter each. To achieve this amount with $1\times10^4$ of target, the magnetic-buoyant separation needs to be approximately 4% efficient (100% efficient separation meaning that all the targets are captured and have a single 10 um particle bound to each). A visual assay with a sensitivity of $1\times10^4$ target could represent a potential 100-fold improvement over the state of the art visual lateral flow assays.

Buoyant Separation

It can be advantageous to isolate cells using only the principles of buoyancy to separate or isolate targets, such as nucleic acids, cells, proteins, etc. As a result, we also describe several buoyant separation devices that can be used manually or in an automated system.

Buoyant separation can be performed in a vial or pipette tip by waiting a short amount of time (0.5-5 minutes) to allow for the beads to float to the top of the vial or pipette tip.

After floating to the top of a vial, the buoyant beads can be isolated from the vial by removing the top layer of fluid that contains buoyant beads and placing them into a new vial. This can be repeated as many times as necessary and can be combined with magnetic separation, if needed.

After floating to the top of a pipette tip, the buoyant beads can be isolated from the rest of the fluid by expelling the fluid (not containing buoyant beads) through the tip of the pipette. The beads can be further kept in the vial tip by using large buoyant beads so that they get clogged at the tip of the pipette, which can later be overcome by expelling the fluid out of the pipette tip at a different rate. This can be repeated as many times as necessary and can be combined with magnetic separation, if needed.

Buoyancy can be used in a steady state manner, where the sample is mixed with the buoyant spheres or is added continuously to the buoyant spheres that are at the top of a container with a hole at the bottom. The rate of addition of fluid can then match the rate of fluid draining the system. However, this occurs in a manner that allows for the buoyant beads to maintain at the top of the vial. This is advantageous because sample can be added in this manner and then can be also washed in the same way. Furthermore, this is simple table-top system that could be used for isolating targets and could further be combined with magnetic separation.

Figure 20:
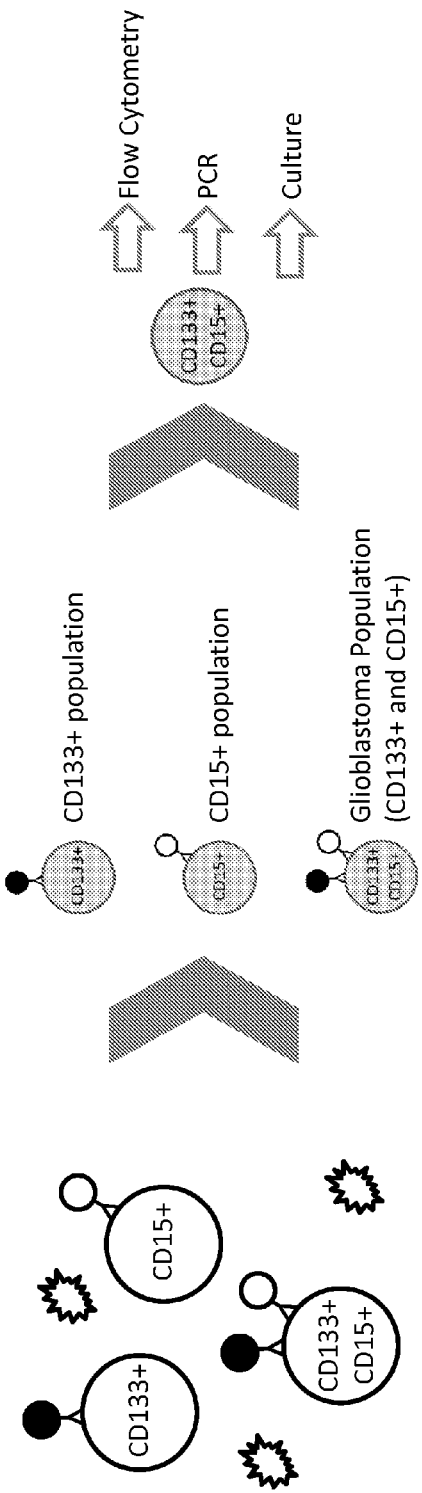
FIG. 20 illustrates an example continuous flow separation process, in accordance with an example.

FIG. 20 illustrates an example process for performing continuous isolation of a multiple cell population, using the example of a glioblastoma cells. At an initial stage, a sample is combined with different beads and corresponding receptor antibodies, for identifying target cells. As shown, a first moiety, e.g., Bead Type 1, associates with a CD133+ antibody and a second moiety, e.g., Bead Type 2, associates with a CD15+ antibody to target different targets. This initial step is a cell labeling step, which, as shown, results in unwanted cells in the sample, as well as singularly expressed cells, either CD15+ or CD133+ expressed cells, all of which, for the present techniques can function as noise in our high specific isolation process. Some cells are expressed by two beads, namely with CD15+ and CD133+ in the illustrated example.

In the next stage, cells are isolated into, in this example, three populations: (i) CD133+ expressed population; (ii) CD15+ expressed population; and (iii) CD133+ and CD15+ dual expressed populations, which in this example correspond to glioblastoma cells.

In a final stage, cells are eluted from the desired population for downstream analysis, e.g., allowing for flow cytometry measure, polymerase chain reaction (PCR) amplification, and/or culturing.

FIG. 21 illustrates an example process for two-bead separation using a single step, in three different types of separation categories. In a first separation category, termed double negative separation, instead of targeting wanted cells, unwanted cells (and or debris) are targeted by the beads. By targeting the unwanted cells, both magnetic and buoyancy separation techniques may be used to separate out the unwanted cells. In some examples, this targeting is single bead specific, to capture a greater amount of the unwanted cells. In other examples, a two bead or other multi bead targeting can be used.

In another example, positive and negative isolation may be performed, where one bead type is to associate with unwanted cells, while the other bead type is to associate with desired targets, e.g., cells.

In yet another example in FIG. 21, three cell populations are captured, such as may result from the process of FIG. 20, but with dedicated separation to for each of the three resulting target types (CD15+, CD133+, and glioblastoma cells).

Example Separation Devices

Figure 22:
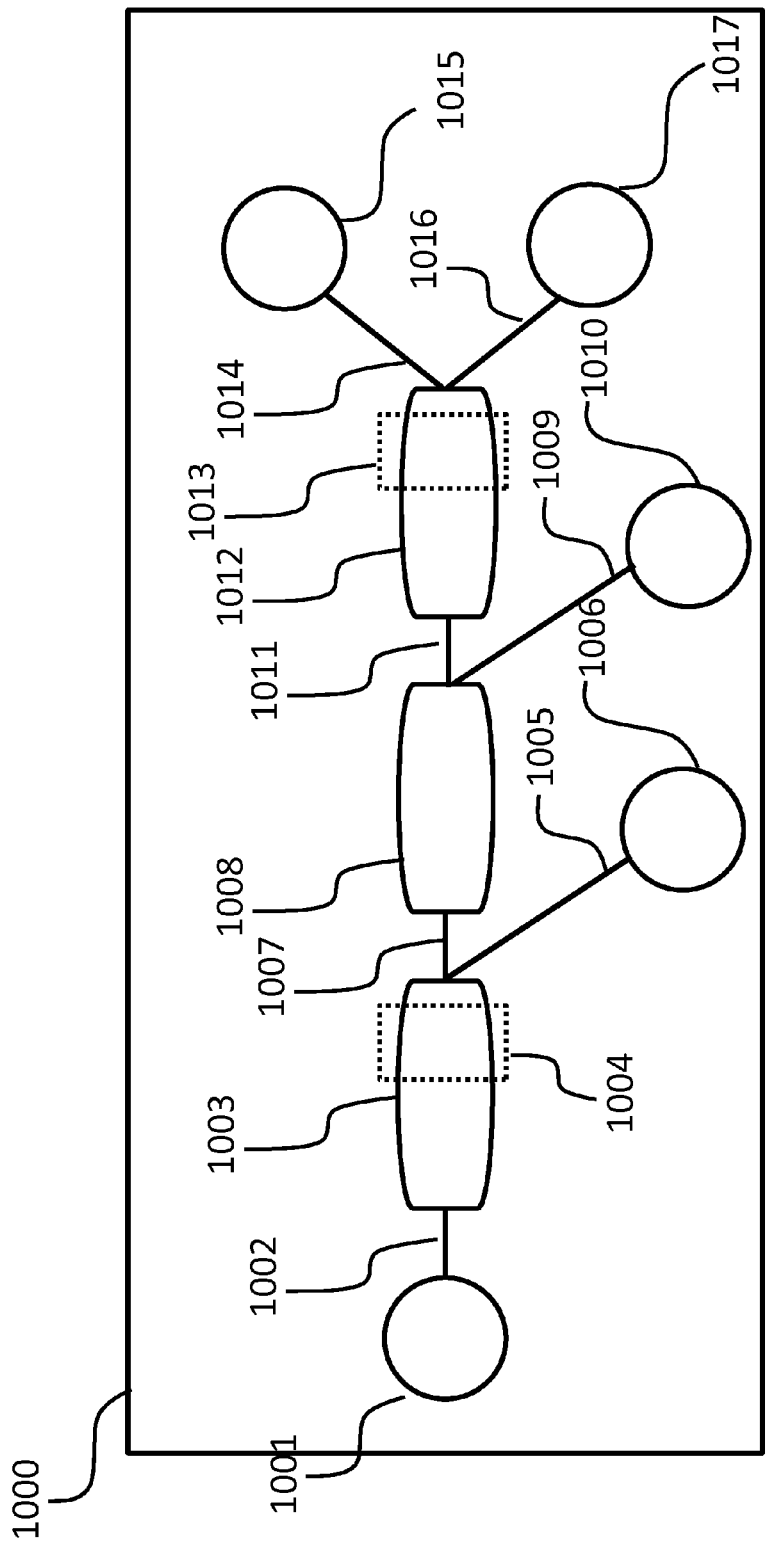
FIG. 22 illustrates an example separation device, in accordance with an example.
Figure 23:
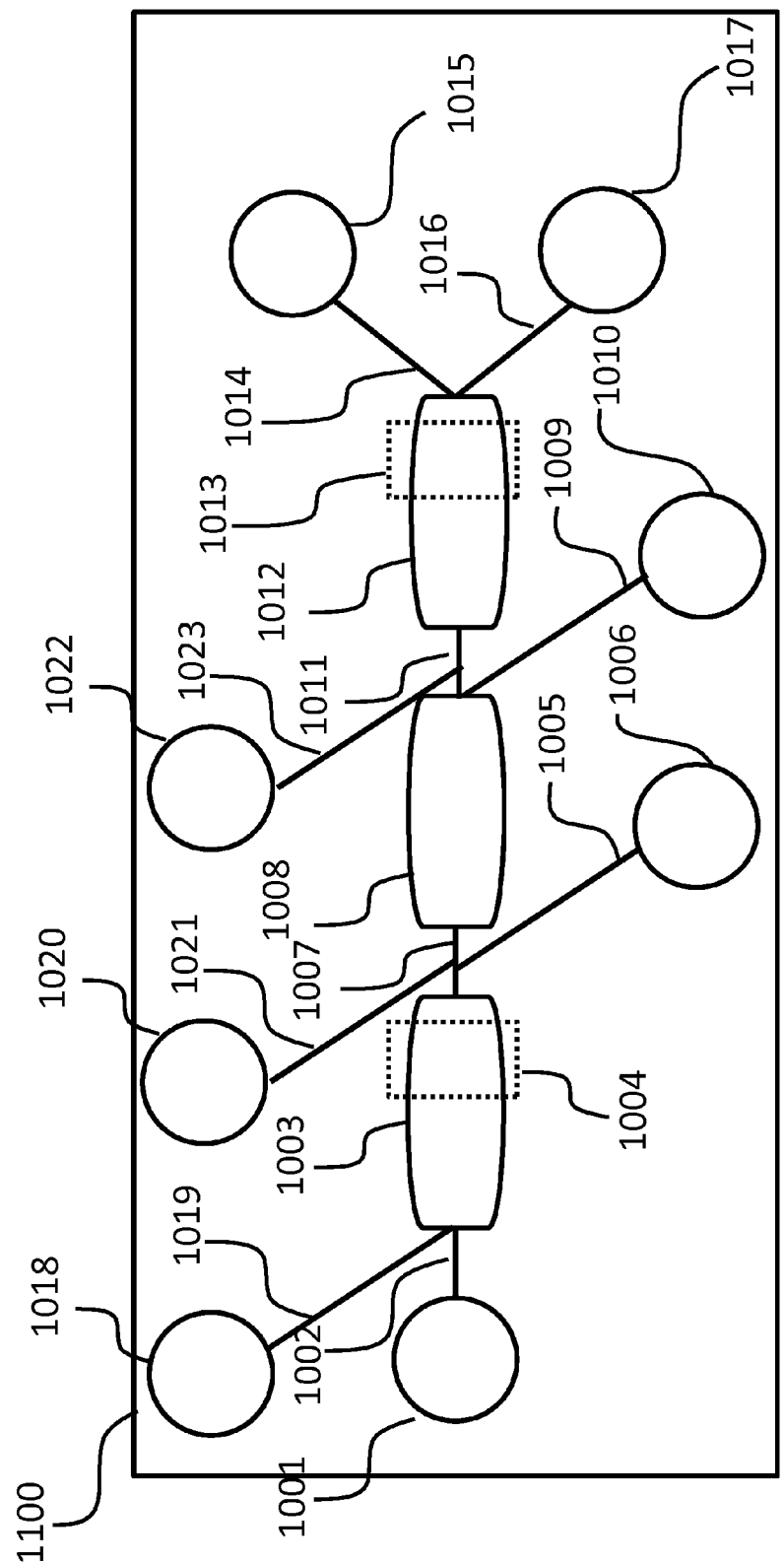
FIG. 23 illustrates an example separation device, in accordance with another example.
Figure 24:
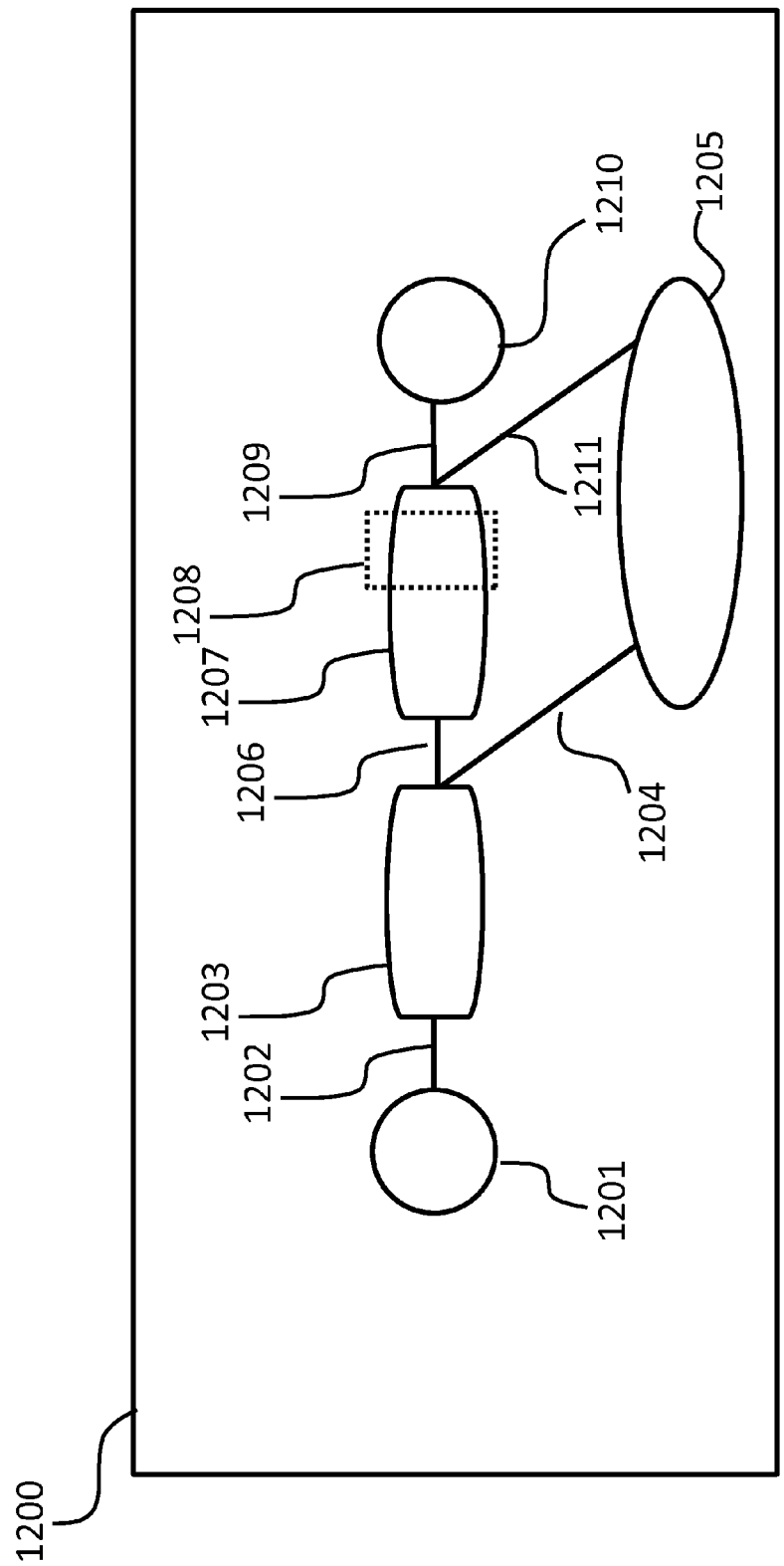
FIG. 24 illustrates an example separation device, in accordance with yet another example.

FIGS. 22-24 illustrate different example separation devices as may be used to implement the present techniques. FIG. 22 illustrates a separation device 1000, which may use a disposable or reusable fluidic chamber. A sample inlet 1001 is coupled to channel 1002 connecting to a first separation chamber 1003, e.g., that is configured to separate unlabeled cells or debris from the rest of the sample (e.g. magnetic beads, buoyant beads, two-bead complexes). In the illustrated example, a magnet 1004 is positioned adjacent to the chamber 1003 and creates a gradient so that magnetic beads flow with the floating fraction (e.g. an upward magnetic force) in the chamber 1003. The chamber 1003 has a branching split so that floating and magnetic fraction continues into the next separation chamber 1008, through a channel 1007, while everything else flows to channel 1005 to an outlet (or reservoir) 1006 for sample measurement and/or testing, or for discarding.

The separation chamber 1008 also uses a branching split to separate the floating fraction, e.g., a buoyant bead expressed target, B+, and a dual-bead expressed target, M+B+, from the sinking fraction (M+). That is, by this separation step, in this example, some of the M+ expressed targets may float, but only if attached to a buoyant bead, which in general shows that additional specificity is still achievable. An outlet 1010 is connected to the chamber 1008 through a channel 1009.

A third stage separation chamber 1012 is coupled to the separation stage 1008 through a channel 1011. The chamber 1012 may be configured to separate the expressed buoyant beads from the magnetic-buoyant complexes (i.e., two-bead complexes), for example, through the use of a magnet 1013 that creates a downward force sufficient to pull the two-bead complexes downward and away from floating fraction, while still flowing to separate outlets. A Branching split into channels 1014 and 1016 is provided, each channel connected to a different outlet 1015 and 1017, respectively. The illustrated two-magnet configuration, and where each magnet is configured to deflect desired sandwich complexes in different directions, can provide further specificity in separation, in part, because the direction of magnetic deflection can depend on upon the buoyancy of the remaining expressed targets in the sample.

The configuration 1000 includes two dual separation stages, corresponding to chambers 1003 and 1013. The stages may offer simultaneous separation or sequential separation. The applied magnetic fields may be varying, to further increase or decrease specificity of the separation process. In some examples, these chambers may be implemented with rotating magnetic field for further AMBR measurement of cell growth.

FIG. 23 illustrates another example separation device 1100, similar to the device 1000, and thus bearing similar reference numerals. The device 1100 further includes, however, inlets 1018, 1020, and 1022 for introducing reagents, through corresponding channels 1019, 1021, and 1023. The reagents may be added to further assist targeting, to assist in flow of sample through device, to accelerate or otherwise assist in removal of non-targets, cells, debris, etc. into the outlet reservoirs, or other control purposes. Example reagents include washing reagents and target detachment buffers.

FIG. 24 illustrates another example separation device 1200 operable for isolating two-bead complexes only. The device 1200 includes an inlet 1201, inlet channel 1202, and first separation chamber 1203, that splits into channels 1204 and 1206, as shown. Two parallel second chambers separation chambers 1205 and 1207 are coupled to the channels respectively, with channel 1205 that receives and contains cells and or debris that were not attached to a buoyant bead or magnetic bead and chamber 1207 that receives buoyant bead expressed targets and magnetic-buoyant bead expressed targets. A magnet 1208 adjacent to the chamber 1207 is used to separate the buoyant bead expressed targets from the magnetic-buoyant complexes (e.g., two-bead complexes), by, for example, creating a downward force sufficient to pull the two-bead complexes downward and away from floating fraction, while still allowing flow. In the illustrated example, a channel 1209 transports the fluid passing through the lower part of chamber 1207 (i.e., the two-bead complexes) to an output (or reservoir) 1210 to hold the isolated target sample. A channel 1211 transports those buoyant beads that were not pulled down by magnet to the chamber 1205.

To better effect separation, in some example devices, an exterior magnet may be used on a translation stage or other assembly to allow that magnet to be brought close to a chamber, moved further away from a chamber, moved up or down a side of the chamber to better control isolation, in particular in a second stage chamber containing both buoyant-only expressed targets and magnetic-buoyant expressed targets.

The flow channels and chambers may be implement through various flow assemblies, including pipettes and vials, and in some examples flow and capture assist features may be embedded in these assemblies. Examples include a ledge within the vial to capture two-bead or buoyant complexes in a unique location within the vial. Also in some examples, the chambers have features such as an angled orientation, tapering sidewalls, etc. to assist in flow into different ones of the branched channels.

In some examples, the devices 1000, 1100, and 1200 may be implemented as part of a fully automated or partially automated process, with separation steps result from executed instructions stored in hardware, software, and/or firmware, including executable instructions stored on one or more computer readable media. Automated processes include, drawing the sample into a pipette and inlet. Moving a magnet into position adjacent a separation chamber. Adjusting the position of the magnet (along the chamber) to control separation, for example, in a closed loop manner, based on measured output specificity. In this way floating fraction separation may be adjustable, during operation. This may be particular useful in that some targets may be expressed by multiple magnetic beads or multiple buoyant beads resulting in certain ranges of buoyancy and magnetism as ideal for highly specific separation. The introduction of reagents, such as target detachment buffers may also be automated.

Whether automatically, partially, or manually, flow rate may be controlled throughout a separation device to better synchronize with buoyant and magnetic separation. For example, for a continuous flow device, an inlet fluid may be added at a certain rate and an outlet fluid collected at a certain rate, where in some examples, the two rates are similar levels. The device may include components to add and remove fluid at controllable rates.

Figure 25:
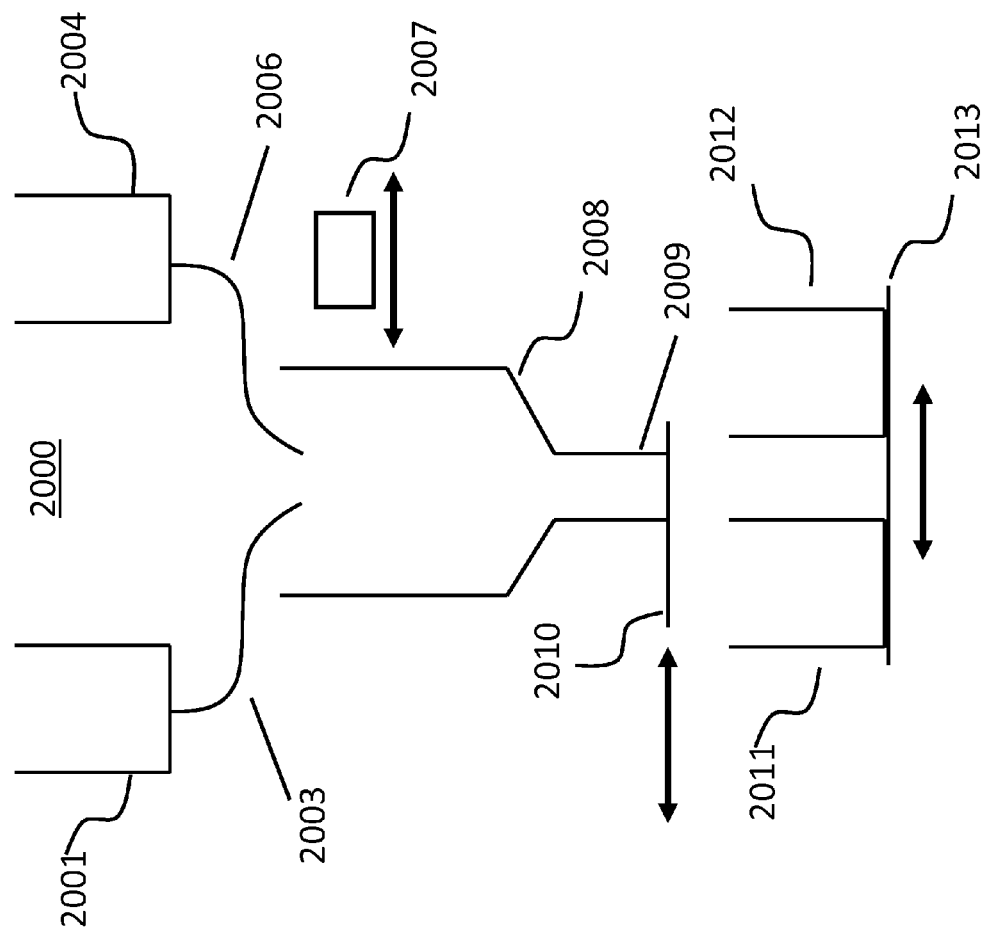
FIG. 25 illustrates a separation chamber and magnet control configuration, in accordance with an example.

FIG. 25 illustrates a flow control configuration 2000 that may be used in an example implementation of the present techniques. A sample container 2001, with flow control valve, is coupled to a flow channel 2003, releasing sample into a buoyancy chamber 2008. A reagent container 2004, with flow control valve, is coupled to a flow channel 2006 also releasing into the buoyancy chamber 2008. Buoyancy separation occurs with the chamber 2008, at a rate dependent upon the flow rates from the containers 2001 and 2004. A position adjustable magnet 2007 is disposed, at least initially, on one side of the chamber 2008, although the position, both vertically and horizontally, may be adjusted depending on the desired location of separation of magnetic-buoyant expressed targets, based on the amount of magnet beads associating with the target, based on the amount of buoyant beads associating with the target, based on the size of the buoyant beads, based on the size of the magnetic beads, based on the size ratio of the magnetic to buoyant beads, based on flow rate, based on the desired buoyancy of the target, based on the desired magnet moment of the target, or any combination thereof, by way of example. An outlet 2009 is used to flow fluid using an on/off valve control 2010 into one of two different capture containers, container 2011 designed to capture an isolate sample and container 2012 designed to capture waster, where the containers 2011 and 2012 may be supported on a movable support structure 2013, adjustable to perform washing steps, isolation steps, or detachment steps with the same configuration.

Figure 26:
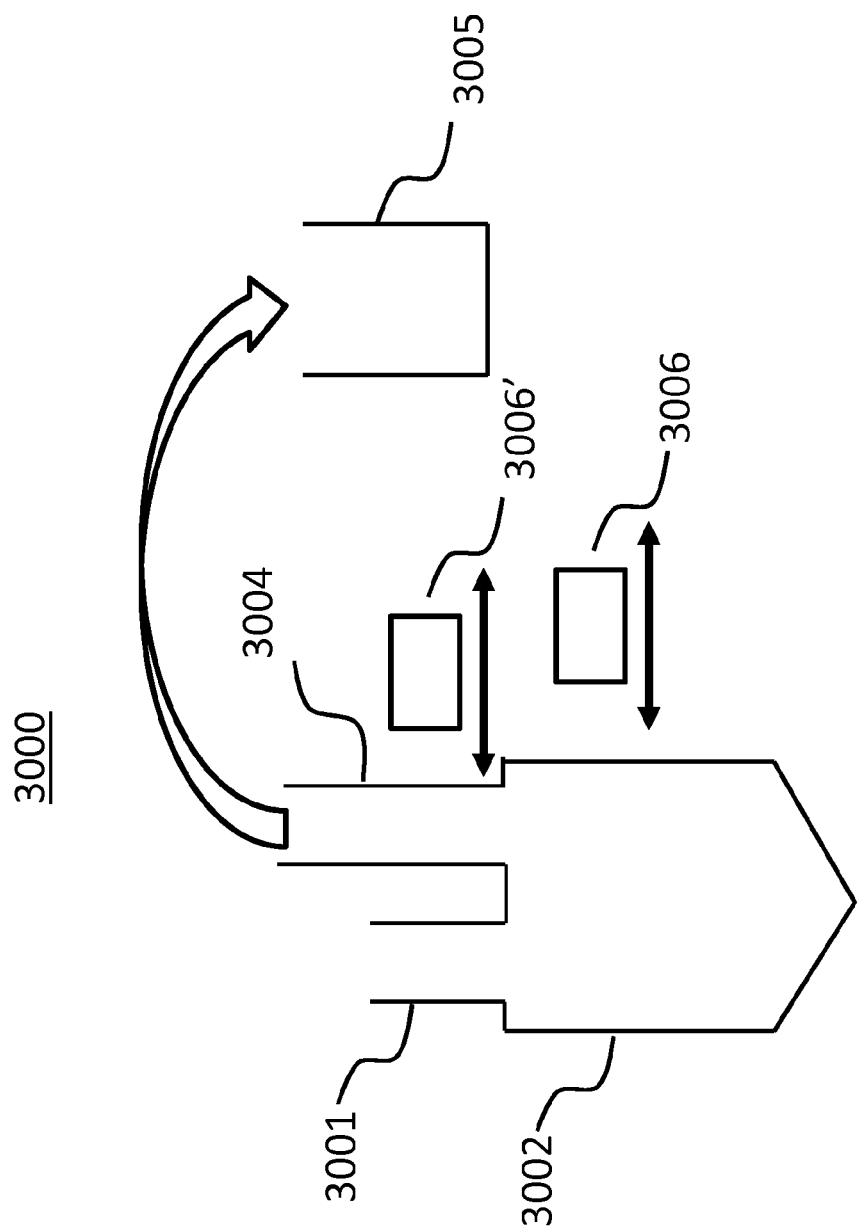
FIG. 26 illustrates a separation chamber and magnet control configuration, in accordance with another example.

FIG. 26 illustrates another example separation configuration 3000 in which a buoyancy chamber 3002 includes an inlet 3001, with or without valve control for controllable flow rate through pressure or gravitational forces. The chamber 3002 may be a sealed chamber so that pressure and fluid flow can be controller. An output channel 3004 is provided, with or without release valve control. A collection chamber 3005 may be coupled to the output channel 3004 for collecting targeted (e.g., two-bead complexes) or non-targets depending on the separation mechanism employed in the chamber 3002. One or more magnets may be used to provide magnetic separation of magnetic-buoyant expressed targets within the chamber 3002. In the illustrated example a magnet 3006 is shown with adjustability vertically and horizontally, where in one position the magnet 3006 is adjacent the chamber body, while in another example the magnet 3006' is adjacent the output channel 3004.

Figure 27:
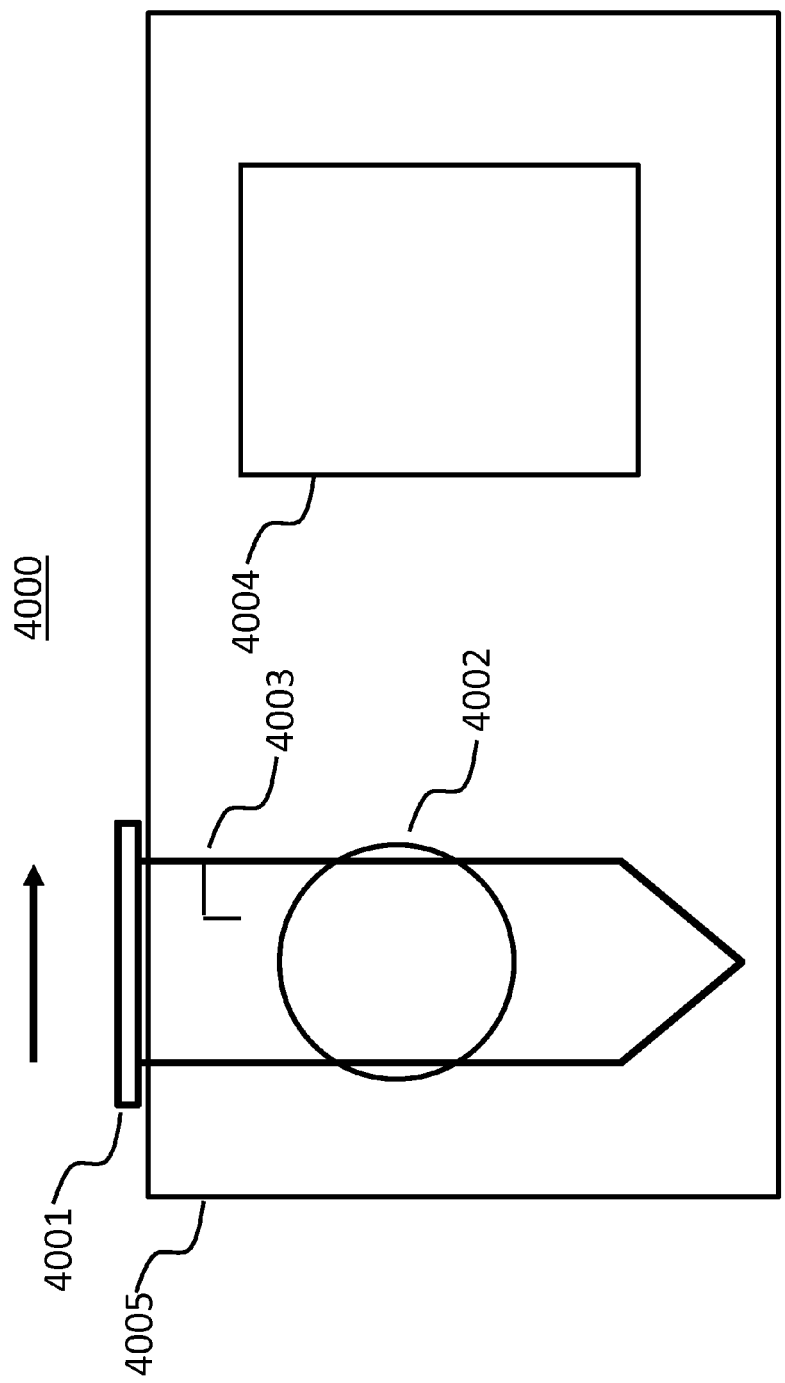
FIG. 27 illustrates a separation chamber and magnet control configuration, in accordance with an example that allows for integration with a visualization or other detection system.

FIG. 27 illustrates a separation device 4000 with an integrated visualization window 4004 positioned to provide access to optically detecting and/or measuring target separation in a chamber 4001, supported on a support structure 4005. An adjustable magnet 4002 is positioned to provide isolation in the chamber 4001, which may include an optional ledge 4003 within the chamber 4001 to catch floating fractions, such as magnet express targets. The chamber 4001 is movable laterally between a hidden position as shown and a visualization position coinciding with the window 4004. The window 4004 may coincide with placement of a light source for excitation or illumination (such as a laser, LED, etc.). The window 4004 may be adjacent a light source on one side of the device 4000 and adjacent a detector on the other side (photodetector, photo-multiplier tube, ccd camera, etc.). This detection mechanism may be used to identify target cells, cell growth, cell response to treatments and reagents, for example.

FIG. 28 illustrates another separation device 5000 having a support 5001, a vial 5002 as a chamber, and a moveable magnet 5004. In this example, the vial 5002 is rotatable within the support 5002. As the vial is rotated, the magnet 4005 may be moved to different locations, for example, from a proximal side position as shown in Position 1 to a distal nadir position in Position 2, for the purpose of allowing the buoyant forces to dominate, as taught herein.

In another aspect of this disclosure, using the methods described herein, enables one to employ a self-assembled AMBR biosensor in a standard well plate format, including a 384 polystyrene microwell plate.

Use of a solid interface provides a more stable environment, where the AMBR sensor is less susceptible to vibration and evaporation. It also allows for much more straightforward and flexible design of disposable testing cartridges. Furthermore, any necessary reagents can be dried down, using long-established and well-known techniques.

One may form magnetic-bead groups (e.g. self-assembled AMBR sensors) that stay together as a unit while rotating at a solid interface. In previous work with self-assembled AMBR sensors, hanging drops were used to solve this issue. However, by use of an array of magnets to pull the magnetic beads into a critical position, magnetic bead groups formed, stayed together as a unit during rotation, and provided signal on a stand-alone prototype system.

Using a solid interface for AMBR sensors also provides the unexpected results of significant reduction in time-to-results. This has been demonstrated by measuring bacterial growth of *E. coli* O157:H7 and *S. aureus* bacteria, when compared to traditional hanging drop AMBR. For comparison purposes, the time to result of performing AMBR measurements at a solid interface were approximately 50 minutes of instrument time, while traditional AMBR required 240 minutes. This is a nearly 5-fold decrease in the time to results, which is quite unexpected.

The use of self-assembled AMBR biosensors was also enabled by using a surfactant in the surrounding medium at a sufficient concentration (i.e., Pluronic F127 at 1%), and by the use of cylindrical wells with a flat bottom. The surfactant prohibited the adherence of the magnetic beads to the bottom of the wells, which otherwise would be a problem. Also, by subjecting the samples to a strong magnetic gradient (achieved by using an array of permanent magnets), magnetic beads assembled into cohesive groups (in the appropriate media), and possessed enough optical asymmetry for straight-forward measurement of the rotation.

When performing solid-interface AMBR, the biosensor speeds up initially before slowing down. This initial speeding up is also unexpected, since AMBR biosensors at water/air and water/oil interfaces do not exhibit this behavior; instead, the rotation period merely slows down due to bacterial growth and an increase in drag. The speeding up at the solid interface happens earlier, and may therefore be used to achieve a reduced time-to-results. For example *E. coli* O157:H7 at a concentration of $5 \times 10^3$ CFU/mL had a time-to-results of 51+/−4 minutes, which is considerably faster than traditional AMBR at water/air interface.

Also described herein are a prototype for the observation of multiple solid-interface AMBR biosensors, and a method for the generation of a suitable rotating magnetic field with 8 mT magnitude and 10 Hz frequency.

Figure 11:
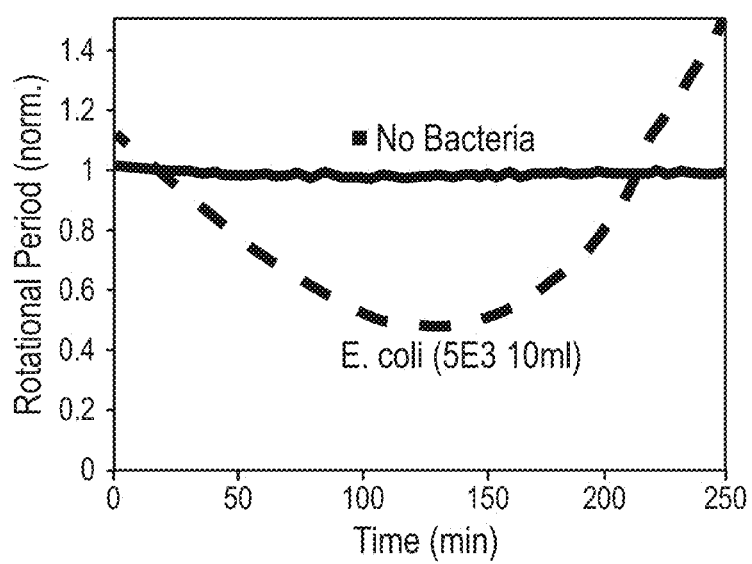
FIG. 11 shows the data of E. coli O157:H7 growth measurements on solid interface AMBR prototype with 10 ml of sample. The overlapping data includes 6 identical data sets from 6 different wells, showing high well-to-well reproducibility. Starting concentrations were $5 \times 10^3$ cfu/mL with a 37 minute sample preparation time. The data is normalized at 25 minutes.

An AMBR biosensor was used on a solid interface, using a group of magnetic beads, and the sensitivity to bacterial growth and overall AMBR behavior was found to be unexpected. In previous AMBR applications at air-water and/or oil-water interfaces, the rotation period of the sensor slows down in response to bacterial growth; however, on solid interfaces there is an additional "dip" in the beginning of the data. Typical results for measuring bacterial growth, using the solid interface AMBR method are shown in FIG. 11, where the initial speeding up and then slowing down can be seen. The initial dip was found to be a result of bacterial growth. This is true since the dip (or the slowing down) was not seen in wells with the same amount of bacteria, but that lacked nutrients (performed in PBS buffer), or contained antibiotics above the minimum inhibition concentrations. Also, the size of the AMBR group did not change significantly under microscopic observation during the speeding up process.

Figure 12:
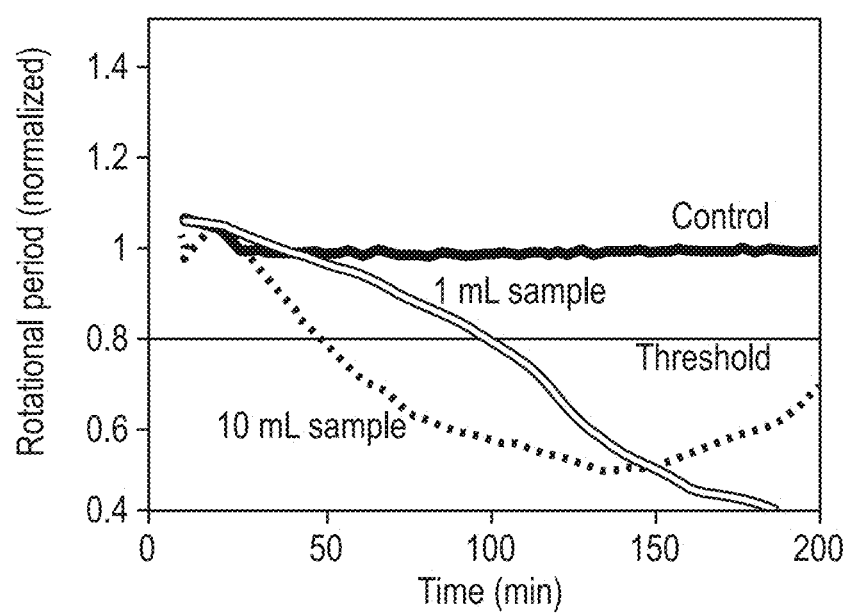
FIG. 12 shows a plot of AMBR results on a standard 384 well plate, comparing $10^6$ beads bound with E. coli at a concentration of $5 \times 10^3$ cfu/mL in either 1 mL or 10 mL of sample.

In the results shown in FIG. 11 and FIG. 12, it is evident that on a solid interface, the rotational period initially sped up in response to bacterial growth—with up to a factor of 2 reduction in the rotational period—before beginning to slow down. The speeding up also happened at an earlier time than the slowing down on air/water and oil/water interface, offering a significant reduction in time to results from 240 min to 86 min for a 1 mL sample of *E. coli* O157:H7 at $5 \times 10^3$ CFU/ml. Additional reduction in time to results was achieved by using larger initial volumes. For a 10 mL sample, the time to results was 51 minutes, this is shown in FIG. 12, where plots for the 1 mL sample, 10 mL sample, and a control sample without cells is shown.

Figure 13:
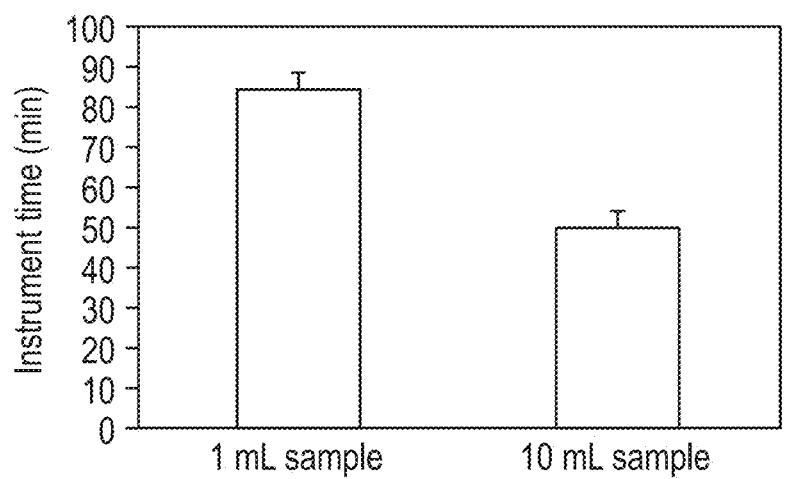
FIG. 13 shows the instrument time for measuring bacterial growth in a standard 384 well plate, using AMBR biosensor with E. coli at a concentration of $5 \times 10^3$ CFU/mL with 1 mL and 10 mL of sample. With 10 mL sample, the CV for time to results across multiple wells was 51±4 minutes, and 86±8 minutes for 1 ml of sample.

FIG. 13 shows the results of the previous paragraph for several wells. The results indicate a relatively small well-to-well variation. FIG. 13 shows the instrument time for measuring bacterial growth in a standard 384 well plate, using an AMBR biosensor on a solid interface with *E. coli* at a concentration of $5 \times 10^3$ CFU/mL. Tests were performed with sample volumes of 1 mL and 10 mL of sample. With 10 mL samples, the CV for time to results across multiple wells was 51±4 minutes and 86±8 minutes for 1 ml of sample.

Figure 14:
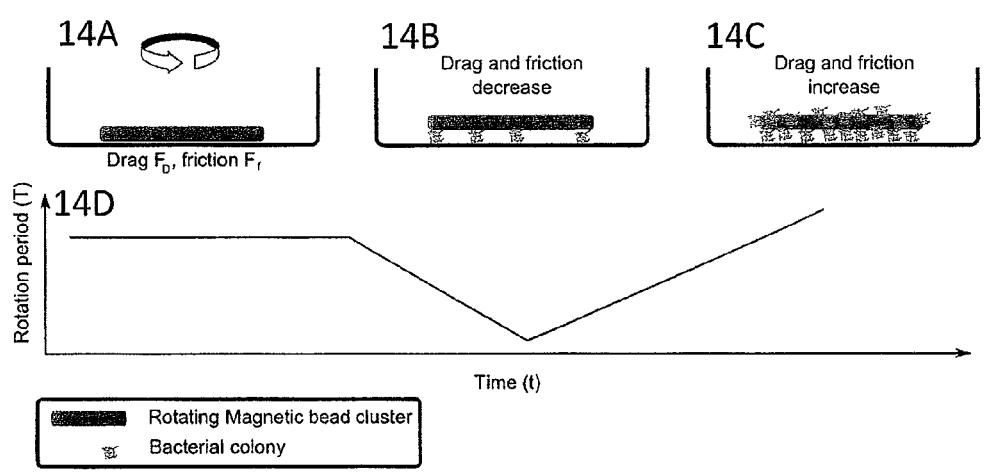
FIGS. 14A, 14B, 14C, and 14D show a schematic overview of an AMBR sensor on a solid interface.

The speeding up behavior was not restricted to *E. coli* O157:H7, or even to gram-negative rods, similar speeding up was observed with Gram-positive coccal *S. aureus* bacteria. The speeding up may be due to colony formation at the bottom of the AMBR group; therefore, reducing friction and/or drag between the rotating group of magnetic beads and the polystyrene well, see FIG. 14 for a schematic representation. FIG. 14A shows a rotating magnetic bead group at a solid interface, which experiences a drag $F_D$. After time passes the bacteria on the bottom of the rotating group may form bacterial colonies, which is shown in FIG. 14B. When this happens the bead group is pushed away from the solid interface, which may reduce the effective viscous drag. This then can lead to a speeding up of the magnetic bead group. Once enough bacterial growth occurs, the size of the magnetic bead group may increase, which is shown in FIG. 14C. This can lead to the traditional slowing down of the rotational period, which is normally observed with air/water interface AMBR measurements. FIG. 14D shows the corresponding rotational period versus time results for FIGS. 14A, 14B, and 14C.

Figure 15:
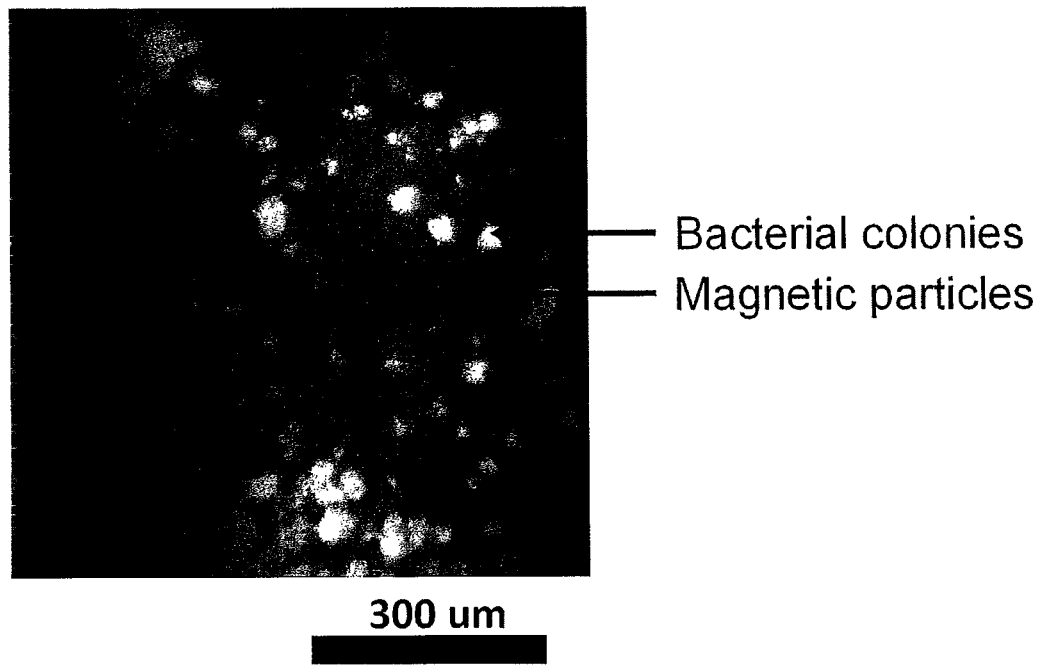
FIG. 15 shows a fluorescent microscopy image of a magnetic bead group with $5 \times 10^3$ CFU/ml of E. coli O157:H7 bacteria, after 250 minutes of rotation on solid interface. Bacteria were stained and therefore appear bright, where magnetic beads form the dark background.

This mechanistic hypothesis was supported by the results shown in FIG. 15, which shows a fluorescent microscopy image of the bottom side of a magnetic bead group at a solid interface after 240 minutes with a starting concentration of $5 \times 10^3$ CFU/ml. The bacteria colonies can be seen as light areas in the image (after live/dead staining).

The results shown in FIGS. 11, 12, 13, 14 and 15 suggest that the presence of cells and their antimicrobial susceptibility can be rapidly detected using AMBR biosensors at a solid interface, using low levels of bacteria. Laboratory measurements have established that the speeding up happens with motile and non-motile, gram-negative and gram-positive cells, and with rod-like and coccal bacteria. Additionally, there is no change in rotational period when an antibiotic above the MIC is used in the surrounding media (0.5 μg/ml gentamicin), or when the media used does not have nutrients available that support bacterial growth (PBS buffer).

Figure 16:
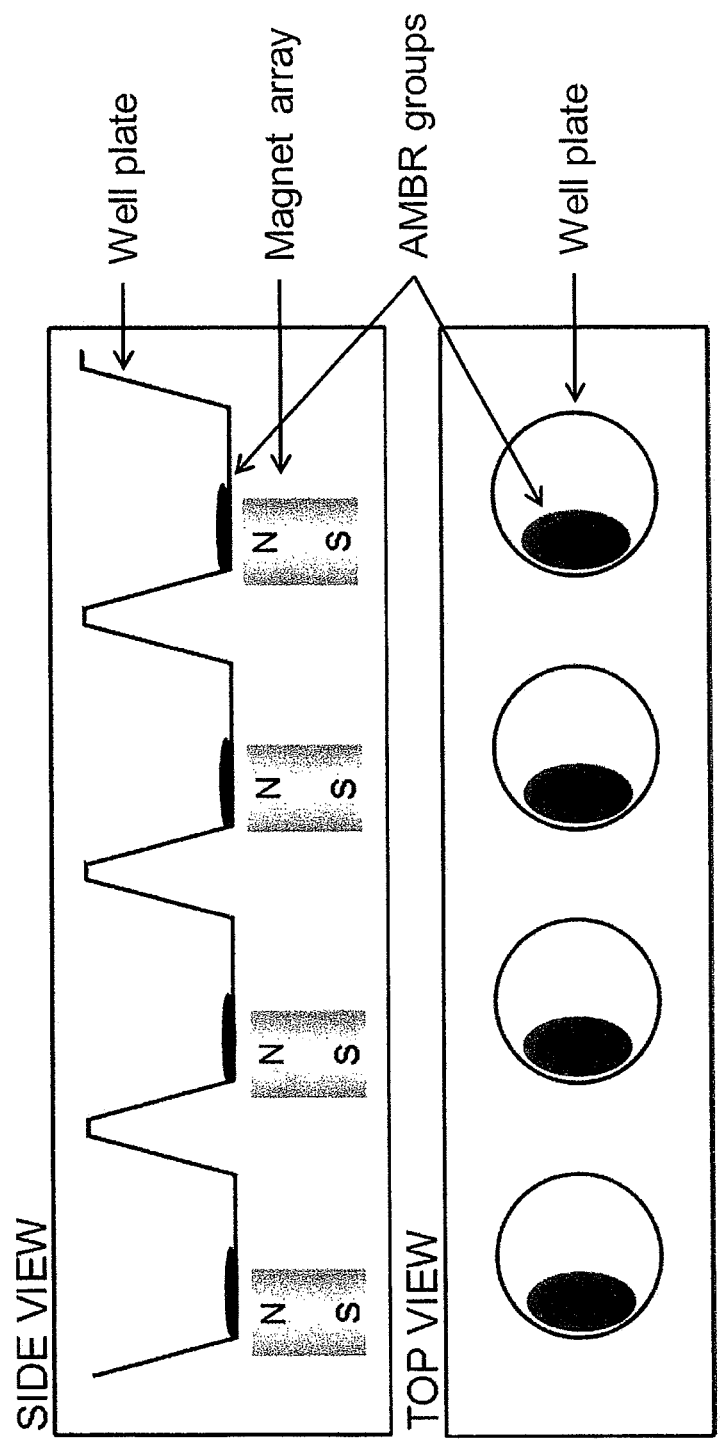
FIG. 16 shows a side view and top view of magnetic bead group formation (self-assembled AMBR biosensor) with a magnet array below the disposable 384 well plate. The drawing is not to scale. The well diameter is 1.8 mm at the bottom of the well.

AMBR biosensors were employed in a standard 384 well microplate, and observed using a custom made 32 well prototype. This was achieved by using round-and-flat bottom polystyrene microplates, where each well was cylindrical with a flat bottom. The tested sample included 3 μm magnetic microbeads and Mueller Hinton II broth (CA-MHB) for microbiology applications, spiked with 1% Pluronic F-127 surfactant to reduce adhesion between magnetic beads and polystyrene. A schematic representation of the formation of the AMBR biosensors in a standard 384 well plate, using a permanent magnetic array can be seen in FIG. 16. When forming the magnetic bead groups at the bottom of the well plate, the position of the magnet can be important. Specifically, robust groups formed when the magnet was off-center from the well plate. Furthermore this positioning helps form groups with optical asymmetry, which is needed for measurements with current prototype designs.

The resulting plate was then placed in a custom made prototype (FIG. 17), and the resulting signal is shown in FIGS. 18A and 18B. FIG. 18A is the raw data input from the photodiode in the prototype, and 18B is the resulting rotational period over 24 hours without bacteria. The flatness of this line indicates the robustness of the rotating group, which allows it to be used as an AMBR sensor.

Figure 17:
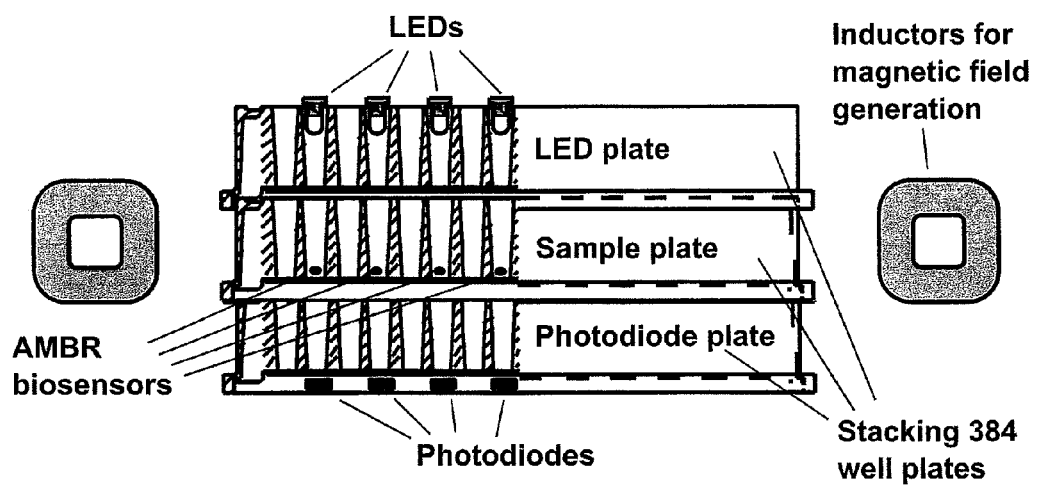
FIG. 17 is a cross section view (side view) of a prototype embodiment used for solid interface AMBR biosensor actuation and measurement. The prototype consists of three sets of standard 384 well plates, which stack on each other, and this stacking is used for alignment. The top plate has 32 LEDs installed in it. The plate is black plastic and has holes drilled at the bottom of each well to let light through. The middle plate is discarded for each test and is made of clear plastic with round and flat bottoms. The bottom plate is black as well (to reduce cross talk between wells) and has photodiodes installed under each 32 wells with a sample. These photodiodes are individually monitored, and the data from one photodiode can be seen in FIG. 18. Surrounding the plate stack are inductors for rotating magnetic field generation—a top view of which can be seen in FIG. 19.
Figure 18:
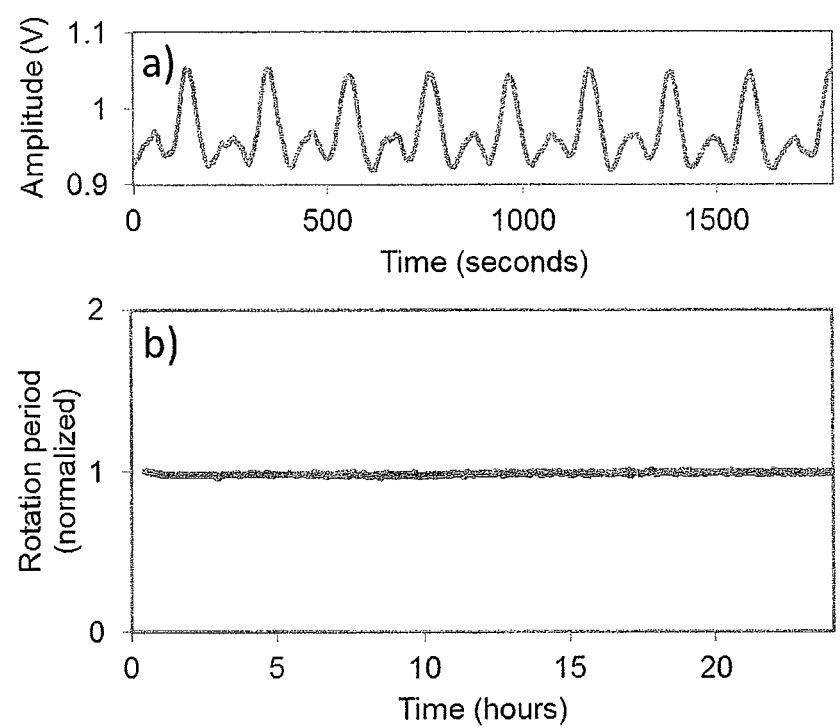
FIG. 18A Shows the intensity variation due to the rotation of an AMBR sensor in a 384 well plate, measured with a photodiode and an LED. The rotational period is calculated from this intensity data.
FIG. 18B shows the rotational period of an AMBR sensor in a 384 well plate over 24-hour period, showing high stability over time.

A cross sectional view of an example prototype device can be seen in FIG. 17, where the prototype consists of three stackable 384 microwell plates. The top plate (LED plate) has 32 LEDs installed to align with every other well. The center plate (Sample plate) is the disposable part, which is loaded with the sample to be analyzed. The bottom plate (Photodiode plate) has a photodiode installed for monitoring the rotation of the AMBR biosensors that takes place in the center plate. The photodiodes are connected to a data acquisition board, which is connected to a computer and analyzed with custom software.

Around the stacked plates, shown in FIG. 17, are the inductors that are used for generating the rotating magnetic field (Inductors for magnetic field generation). The top view of the inductor setup can be seen in FIG. 19. By arranging eight inductors in the shown manner, and connecting Phase A to amplified sine-wave generator and Phase B to amplified cosine-wave (or vice versa), a large and uniform rotating magnetic field can be generated that covers the area of a standard micowell plate. The inductors may be connected in series or parallel.

Protocols for Self-Assembled AMBR on a Solid Interface

In FIGS. 11, 12, 13, 15 and 18 the following protocols were used, unless otherwise noted: Bacterial isolates were obtained from ATCC and stored according to supplier suggestions, *E. coli* O157:H7 (ATCC 35150) and *S. aureus* (ATCC 27660). Before each experiment, 2-3 bacteria colonies were suspended in CA-MHB (Cation-Adjusted Mueller Hinton broth) and grown up to log phase and diluted to 0.5 McFarland standard concentration, which roughly corresponds to $10^8$ CFU/ml. Bacteria were then diluted to the desired concentration.

Anti-*E. coli* O157 functionalized, 2.8 μm diameter magnetic particles (20 μl, Invitrogen 710-03) were mixed with bacteria diluted to $10^4$ CFU/ml (0.9 ml), and allowed to incubate (10 min at 37° C.) with end-over-end agitation. Magnetic separation was performed 3 times and the sample was resuspended in 1 ml of CA-MHB (160 μl). Samples were then pipetted into 384 microwell plate (18 μl each well, Greiner Bio-One 384-Well Small Volume™ Assay Plate (788101)), and the plate was set on a permanent magnet array for 5 minutes to form magnetic bead groups, see FIG. 16. The plate was then placed in a custom made prototype device for observation, shown in FIG. 17. For colony counting, the samples were diluted appropriately, plated on a MH plate and the colonies were counted 18 hours later to obtain accurate bacterial concentrations and magnetic separation capture efficiencies. Total sample preparation time was <40 minutes.

The prototype, shown in FIG. 17, was placed in a laboratory incubator which was set to 37 deg C. The prototype consisted of an LED (350-2318-ND) on top of each well and a photodiode (TSL257) underneath, which was used to measure fluctuation of the passed light that resulted from the rotation of the AMBR biosensors. The signals were acquired with four low cost data acquisition boards (NI 6008) using a custom made LabView executable. The prototype shown in FIG. 17 was used to perform 109 experiments between May 16, 2011 and Dec. 15, 2011, and it was running 5174 hours during that period.

Figure 19:
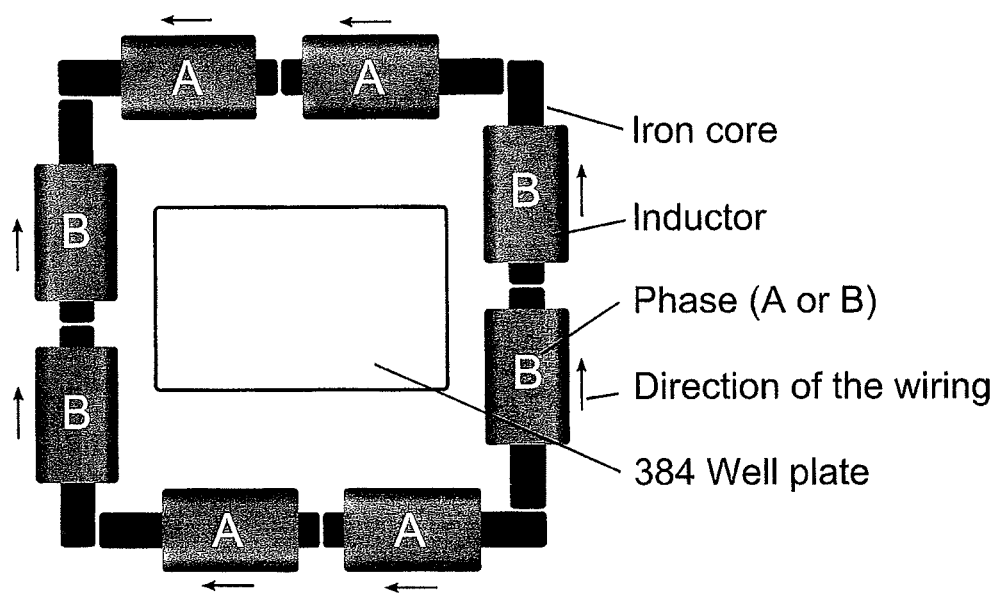
FIG. 19 shows the top view of the AMBR solid interface prototype, including a rotating magnetic field generation setup. The setup uses standard off-the-shelf components, the main parts being iron core inductors and a stepper motor driver used to drive them. A rotating magnetic field spanning across standard well plates up to 10 Hz and 10 mT can be generated with this device.

The rotating magnetic field for the prototype was generated using a setup shown in FIG. 19. The rotating magnetic field (7.9+/−1 mT, 10 Hz) was generated using a stepper motor driver (Gecko 201X), and eight 10 mH core inductors, shown in FIG. 19 (ERSE Audio, Model: ELC54-19-10000) assembled around the stacked well plates. The stepper motor driver was powered with a power supply (48V, 1 A), and saw-tooth signal (5V, 2.5 mA) with 40 times the frequency needed for the rotating magnetic field, in this case 400 Hz saw tooth signal for 10 Hz rotating magnetic field.

While the methods, devices and systems have been described in some detail here by way of illustration and example, such illustration and example is for purposes of clarity of understanding only. It will be readily apparent to those of ordinary skill in the art in light of the teachings herein that certain changes and modifications may be made thereto without departing from the spirit and scope of the invention.

What is claimed is:

1. A method of forming, manipulating and isolating a sandwich complex, wherein the complex consists of one or more magnetic beads, one or more buoyant beads, and a target analyte, and where the one or more buoyant beads in the complex provide sufficient buoyancy such that the complex floats, the method comprising:
    (a) contacting the sample in a solution with (i) a population of the one or more magnetic beads, each magnetic bead comprising a moiety that can specifically associate with the target analyte under appropriate conditions and (ii) a population of the one or more buoyant beads, each buoyant bead comprising a moiety that can specifically associate with the target analyte under appropriate conditions, wherein contact results in formation of the complex containing the one or more magnetic beads, the one or more buoyant beads, and the target analyte, such that the complex is both magnetic and buoyant; and
    (b) isolating the complex based on the combined movement of the complex in a magnetic field and in a gravitational or centrifugal field.

2. The method of claim 1 wherein the magnetic bead moiety and the buoyant bead moiety are different.

3. The method of claim 1, wherein the magnetic bead and the buoyant bead are added to the sample sequentially.

4. The method of claim 1, wherein the magnetic bead is added prior to addition of the buoyant bead.

5. The method of claim 1, wherein the magnetic bead moiety and/or the buoyant bead moiety is selected from the group consisting of a protein, a charge and a nucleic acid.

6. The method of claim 5 wherein the protein is an antibody.

7. The method of claim 1, wherein the target is selected from the group consisting of a cell, a protein, a nucleic acid and a small molecule.

8. The method of claim 7 wherein the cell is a eukaryotic cell.

9. The method of claim 7 wherein the cell is a prokaryotic cell.

10. The method of claim 1, wherein the magnetic bead and/or the buoyant bead are removed following isolation of the target.

11. The method of claim 1, wherein the magnetic bead moiety and/or the buoyant bead moiety comprises a detectable label.

12. The method of claim 1 further comprising removing the magnetic bead and/or the buoyant bead that is not associated with the target from the sample.

13. The method of claim 1 further comprising removing the magnetic bead and/or the buoyant bead that is associated with the target from the sample.

14. The method of claim 1 further comprising an additional buoyant bead comprising a moiety that can specifically associate with a target, wherein the buoyant bead and the additional buoyant bead have different buoyancies relative to each other.

15. The method of claim 1, wherein the movement in the magnetic field and the gravitational or centrifugal field are performed simultaneously.

16. The method of claim 1, wherein the movement in the magnetic field and the gravitational or centrifugal field are performed separately.

17. The method of claim 16, wherein the complex is subjected to the magnetic field prior to being subjected to the gravitational or centrifugal field.

\* \* \* \* \*